(12) United States Patent
Niebling

(10) Patent No.: US 11,690,890 B2
(45) Date of Patent: Jul. 4, 2023

(54) KITS FOR MANUFACTURING INHALABLE FORMULATIONS OF MEDICINAL CANNABIS COMPOUNDS FOR AEROSOL DEVICES, APPARATUSES, AND METHODS FOR MAKING AND USING THE SAME

(71) Applicant: Avram Niebling, Portsmouth, NH (US)

(72) Inventor: Avram Niebling, Portsmouth, NH (US)

( * ) Notice: Subject to any disclaimer, the term of this patent is extended or adjusted under 35 U.S.C. 154(b) by 1056 days.

(21) Appl. No.: 16/352,998

(22) Filed: Mar. 14, 2019

(65) Prior Publication Data

US 2020/0288786 A1    Sep. 17, 2020

(51) Int. Cl.
| | | |
|---|---|---|
| *A61K 9/00* | (2006.01) | |
| *A61K 31/352* | (2006.01) | |
| *A61K 36/73* | (2006.01) | |
| *A61M 15/00* | (2006.01) | |
| *A61M 15/06* | (2006.01) | |
| *A61M 16/00* | (2006.01) | |

(52) U.S. Cl.
CPC ............ *A61K 36/73* (2013.01); *A61K 9/0073* (2013.01); *A61K 31/352* (2013.01); *A61M 15/0028* (2013.01); *A61M 15/06* (2013.01); *A61M 16/0006* (2014.02)

(58) Field of Classification Search
CPC .... A61K 9/0073; A61K 31/352; A61K 36/73; A61M 15/0028; A61M 15/06; A24F 40/10; A24F 40/42
See application file for complete search history.

(56) References Cited

U.S. PATENT DOCUMENTS

| | | | |
|---|---|---|---|
| 2017/0233114 A1* | 8/2017 | Christensen | .............. B65B 3/14 141/2 |
| 2018/0263283 A1* | 9/2018 | Popplewell | .......... A24B 15/167 |
| 2018/0325175 A1* | 11/2018 | Sudlow | ................ B67D 7/0205 |

FOREIGN PATENT DOCUMENTS

WO    WO2017180660    * 10/2017

* cited by examiner

*Primary Examiner* — Mina Haghighatian
(74) *Attorney, Agent, or Firm* — Steven M. War, Esq.; War IP Law, PLLC

(57) ABSTRACT

Kits enabling an end user to efficiently compound inhalable formulations containing medicinal compounds, for use in in aerosol device (e-cigarette; personal vaporizer). Kits include a reusable storage device, a filling station, at least one predetermined amount aerosol precursor in a container and at least one empty cartomizer (cartridge) for use in an aerosol delivery device. Optionally, kits may also include a predetermined amount of extract containing a known amount of medicinal compound, enabling the production of an amount an inhalable formulation. Optionally, kits may contain amounts of inputs that enable the refilling/reuse of cartridges.

7 Claims, 15 Drawing Sheets

FIG. 5
FIG. 6
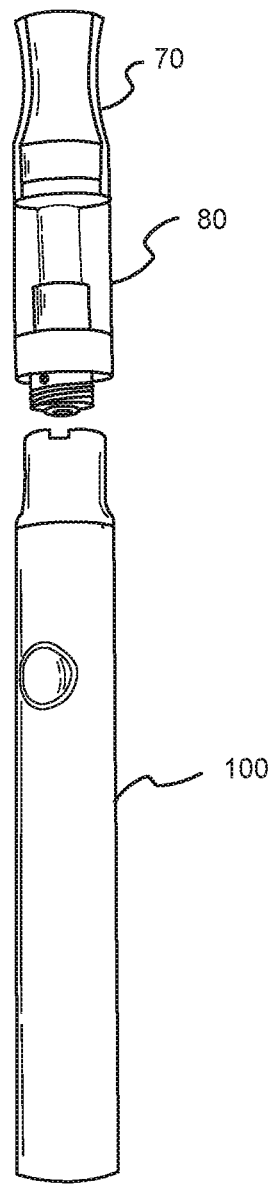
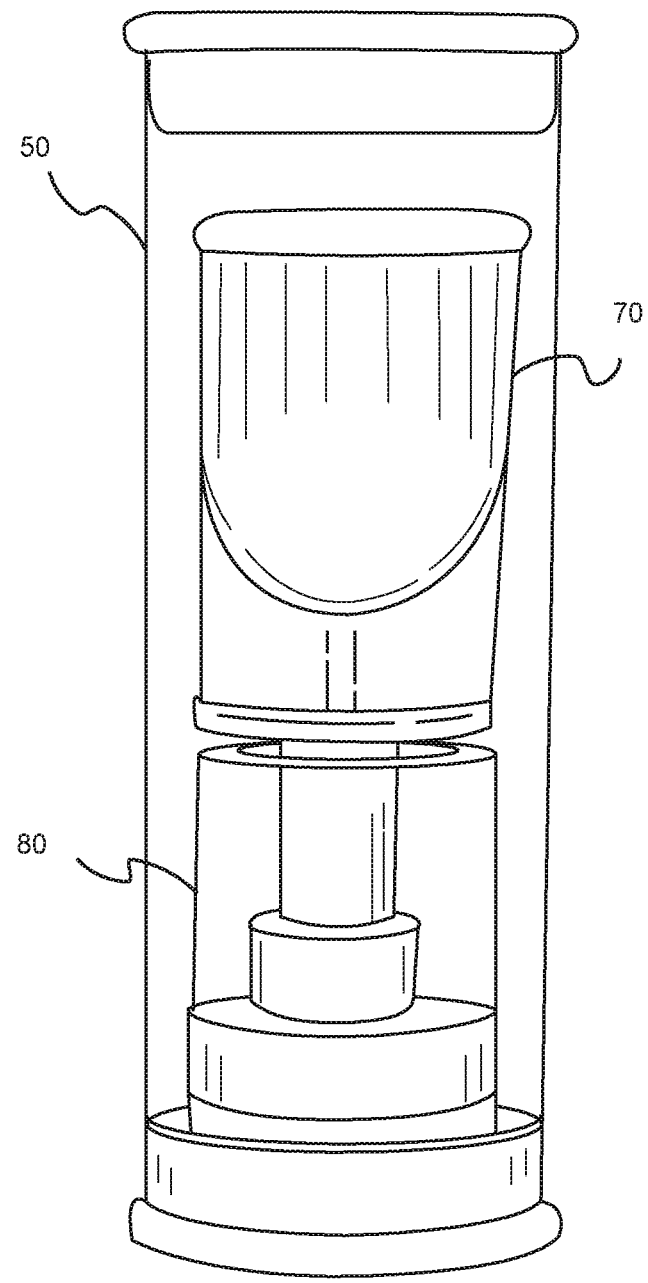

FIG 9
FIG 10
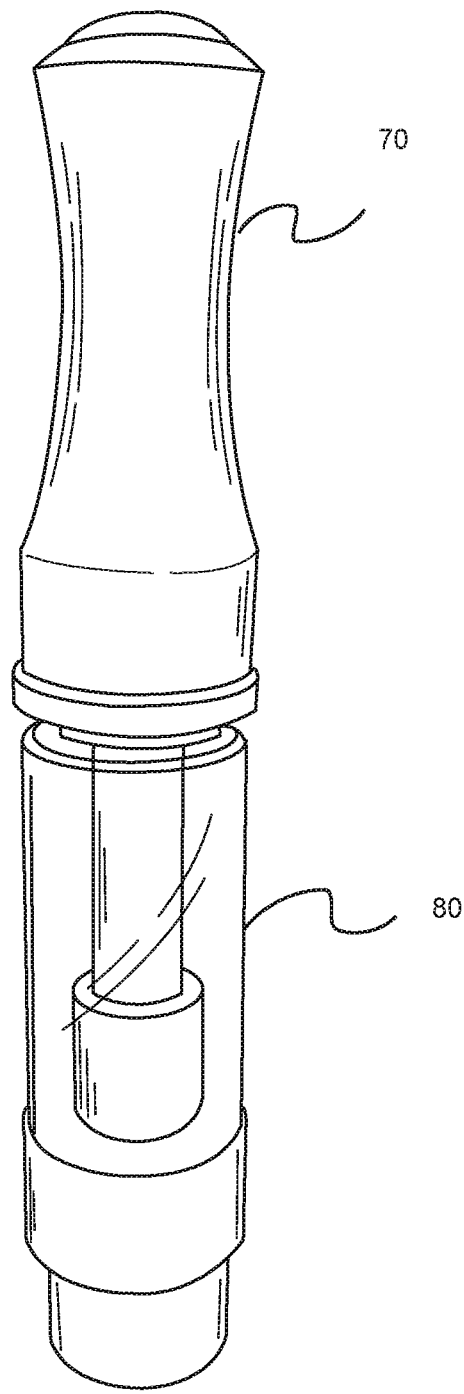
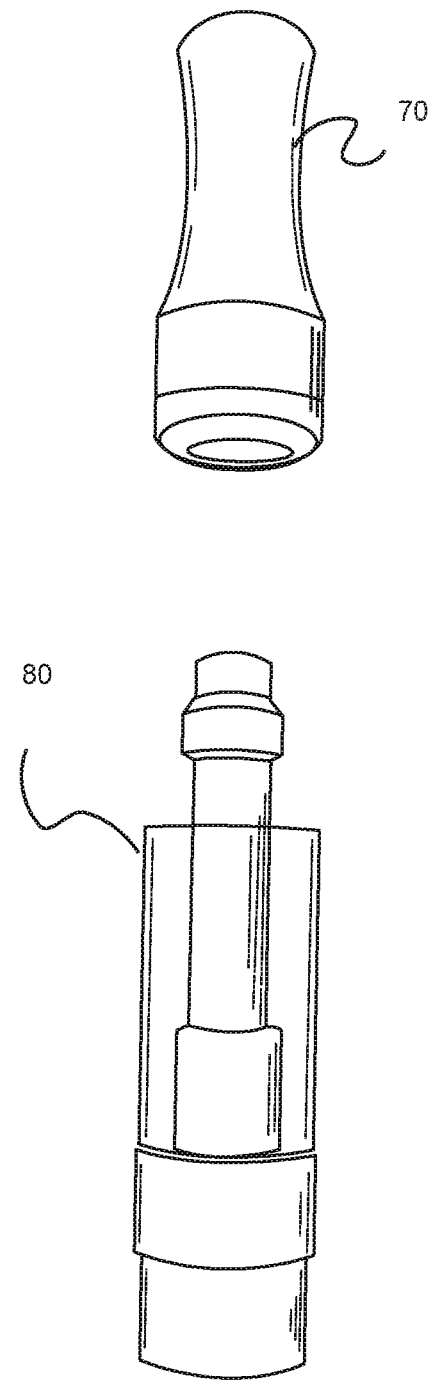

KITS FOR MANUFACTURING INHALABLE FORMULATIONS OF MEDICINAL CANNABIS COMPOUNDS FOR AEROSOL DEVICES, APPARATUSES, AND METHODS FOR MAKING AND USING THE SAME

BACKGROUND OF THE INVENTION

1. Field of the Invention

The present invention relates generally to vaping, aerosol devices, and inhalable formulations of medicinal compounds.

2. Description of the Prior Art

U.S. Pat. No. 6,041,789 discusses that vaping traditionally has been associated with the use of e-cigarettes, which were developed as an alternative to traditional cigarettes as a means for volatizing active components, particularly nicotine, for inhalation without combustion, while at the same time providing the user with an oral experience similar to that of traditional cigarette smoking. Electronic cigarettes are also known as Personal Vaporizers (PV) or aerosol delivery devices.

Aerosol delivery devices have three fundamental parts: a formulation storage component often known as a reservoir or tank, which generally includes a detachable mouthpiece, an atomizer which serves as the heating element responsible for atomizing the formulation into an inhalable mist, and a battery unit that provides power to the atomizer, which contains a coil that heats up and volatizes the formulation into an inhalable mist. A 'cartridge' or 'cartomizer' or 'clearomizer' component has been developed to brings the separate reservoir and atomizer component together in a single integrated component. Cartridges can be disposable or refillable.

U.S. Pat. No. 9,687,027 B2 presents a cartridge that is compatible/adaptable for use with range of pharmaceutical compounds or synthetic compounds which are capable of being vaporized (or volatilized) at a relatively low temperature and without harmful degradation products for use with personal vaporizers (also referred to as aerosol delivery devices).

Patent Document No. WO2015117243A1 discusses a formulation derived from cannabis extracts.

U.S. Pat. No. 9,609,893 B2 discloses a personal vaporizer system with a 'detachable' cartridge. Cartridges can be disposable or refillable. Patent Document No. CN206687159 U discloses a detachable, refillable cartridge.

U.S. Pat. No. 9,420,829 B2 discloses a wick that can be adapted for use with e-liquids with different physical properties.

U.S. Pat. No. 9,888,722 B2 discloses a cartridge that contains an atomizer unit that can be adapted for e-liquid viscosity to assure a better e-liquid gliding effect.

U.S. Pat. No. 9,271,529 B2 discloses a cartridge that is optimized for low viscosity e-liquids derived from a plurality of substances (non-nicotine use cases).

U.S. Pat. No. 9,955,737 B2 notes that differences between atomizers cause differences in the ingredients and their concentrations delivered to users, even when the same liquid is used. This document also discloses two styles of cartridge: 'bottom coil' and 'top-coil' which each have fundamentally different atomizer assemblies and filing methods.

Automated cartridge filling technology is disclosed in U.S. Pat. No. 9,668,520 and Patent Document No. WO2016200253.

Patent Document No. WO2016064987A1 highlights a cannabis extract with medicinal benefits.

U.S. patent Ser. No. 14/206,942 discloses that some 1% by weight of the plant is composed of a mixture of twenty flavonoid compounds which are well known as antioxidants and which also scavenge damaging free radicals.

Patent Document No. WO2018148152A1 discloses terpene-based compositions which relate to enriched formulations that are biomimetic to the aroma, flavor, and pharmaceutical effect of various biochemicals naturally present in particular strains of the Cannabis plant, including terpenes and cannabinoids Patent Document No. WO2016019353A1 discloses some of the medical benefits attributable to one or more of the cannabinoids isolated from cannabis.

U.S. Pat. No. 7,105,685 discloses cannabinoids for the treatment of diseases associated with immune dysfunction, particularly HIV disease and neoplastic disorders.

SUMMARY OF THE INVENTION

Discussion of the Prior Arts' Failure to Meet the Current Needs of the Market and the Development of the Present Invention Increasingly inhalable formulations for use in aerosol generating devices are being created to deliver active/medicinal compounds other than nicotine, to deliver inhaled doses of the medicinal compound. For example, the use of active compounds in cannabis, known as cannabinoids, which have been shown to have an array of medicinal properties, are being increasingly recommended by healthcare providers to their patients, largely due to their effectiveness as compared to other methods of cannabis compound ingestion. Inhalation of medicinal cannabis compounds through vaporization has shown to provide more consistent, controlled, and immediate effects as compared with smoking marijuana leaves and buds directly and eating edible forms of the compound. For example, with smoking, up to 40% of the available cannabinoids may be biologically unavailable due to combustion and sidestream smoke. When medical cannabis compounds are consumed in food, it is also difficult to gauge the amount consumed and/or its effects. Depending on an individual's digestive process, many medicinal cannabis compounds can break down prior to reaching the bloodstream, causing a significant reduction in the therapeutic effectiveness or potency of the medicine.

As cannabinoids are increasingly understood for their medicinal qualities and vaporization continues to be recognized as a highly effective delivery method for many patients and users seeking that medication, the scope (production and variation) and importance of inhalable cannabinoid formulations is increasing. As such, there is an increased need for systems that enable the controlled production and delivery of cannabinoid formulations via aerosol devices. Given fragmentation of state laws and regulations around the production and use of cannabinoid containing formulations, many pharmacists, patients and anyone else prescribing or consuming said formulations for medicinal use (controlled doses) have an increased need to understand the properties and methods of producing and delivery said formulations. Due to numerous factors (principally the treatment of cannabis compounds as a Schedule 1 drug) the method/practice of filling cartridges—creating inhalable formulations and pairing with a delivery device—has, to date, largely been defined by black market/recreational use cases and participants. However, 'filling cartilages' is fast becoming a more specialized, medical/pharmaceutical practice.

The process for optimizing the delivery of medicinal compounds like cannabinoids via vaporization is function of multiple variables; the properties of the inhalable formula, the properties of the cartridge/device component, including the battery power to the cartridge, and filler preferences like potency and flavors.

There are a wide range of different formulations can be used for delivering medicinal benefits via aerosol delivery devices, and different formulations contain a different compounds that, when combined, have fundamentally different properties, such as its density, viscosity, surface tension and vapor pressure (patent ref). Typically, the formula for an inhalable cannabis solution includes a cannabinoid carrying extract and a non-active additive that may be a base carrier liquid, diluent, or flavor and effect inducing-additive like terpenes.

Extracts

It's important for the end user to understand that cannabinoid extracts, which include THC and CBD, may contain different amounts of an organic solvent used during the extraction process. As such, cannabinoid extracts may take a variety of formats and have varying levels of purity. Extracts may require different precursors/additives and methods of mixing to generate viable formulations for use in a particular device, which may be optimized for a particular viscosity of liquid formulation. 'Unwinterized' cannabis extracts containing higher amounts of lipids and waxes and other plant constituents which are not oil soluble, generally require more additives (carrier liquid) to reach a suitable liquid state for inhalation, whereas 'winterized' extracts are more refined an have higher potencies and need less additives to be inhaled via aerosol delivery device. Extracts may contain varying levels of other compounds found in cannabis, like flavonoids and terpenes. These compounds are known to synergize with cannabinoids to provide unique medicinal outcomes, vs ingesting the cannabinoid alone. Typically, the more refined an extract is (despite the high potency/cannabinoid concentration), the more of the naturally occurring other compounds are removed in the extraction process.

Diluents

Also known as carrier liquids and diluents, aerosol precursors typically used in the production of cannabis-based formulations include PG/VG, PEG, MCT oil, and terpene-blends (generally flavorless). Additives may be introduced in varying ratios to adjust the properties, such as the viscosity, of the formulation to enable atomization of the formula in an aerosol device.

Flavorants

Other compounds, some of which may be sourced from cannabis, known as terpenes, are increasingly popular inputs in cannabis-based inhalable formulations. They may provide other effects in addition to those produced by ingestion of cannabinoid concentrations. Terpenes are also being used increasingly to reduce the viscosity of cannabis extracts and provide added medicinal value. Non-flavored terpenes may be considered diluents by many skilled in the art. Other flavoring solutions exist, such as those typically used in traditional nicotine e-liquids.

Mixing/Filling

To create a suitable inhalable formulation from cannabinoid extracts, the extract is typically combined with an aerosol precursor (carrier liquid/solvent/diluent) and heated to ~150 F and stirred until the mixture reaches a homogeneous state with desired properties. Those skilled in the art know that a variety of solvents and mixing methodologies may be utilized to deliver an effectively mixed formula. such as a hot plate, microwave, or placing a container in hot water. Once the formulation has reached a suitable state, it can be injected into a cartridge, for use in an aerosol generating device. Some cartridge models have unique filling instructions. Most recommend that, after the cartridge has been capped with its mouthpiece, it should be turned upside down for at least twelve hours to reduce potential leakage.

As mentioned above, the effective delivery of medicinal compounds like cannabinoids via vaporization is not only a function of creating a specific inhalable formulation (usually a liquid), it also involves identifying a cartridge/device component that is suited to deliver the formulation in the intended way. Concurrently, aerosol generating devices have a constructions and battery/power levels that are optimized for vaporization of pre-vapor formulations with fairly specific properties, including such as its density, viscosity, surface tension and vapor pressure. If the inhalable formulation is not optimized for the design/properties of the aerosol delivery device being used, the delivery of the medicinal compounds in controlled doses can be easily compromised. The size of the inlet holes in cartridge atomizer, for example, determine the flow rate of a particular formulation housed in the tank of the cartridge. The intake holes control the flow rate of the formulation to the atomizer coil. If the viscosity of the formula is too high or too low, the end user will experience a suboptimal vaping experience (potentially burning taste, low vapor production, or flooding, or even complete failure of the device). The battery power and resistance of the atomizer in a cartridge also impacts the performance (principally by affecting the temperature of the coils in the cartilage that atomize the formulation into inhalable units) of a delivery device in providing a controlled, targeted amount of medication. For example, it has been shown that high volatizing temperatures can degrade some medicinal compounds found in cannabis-based inhalable formulations. Often times, temperature can be controlled by reducing the voltage/power level on a battery until you reach a desired vaping outcome.

Thus, there is a significant amount of trial and error for those trying to create and deliver targeted (and possibly prescribed) inhalable formulations containing cannabis derived medicines. This has important implications for those that create formulas and for those that consume the medicine. It's important the producer creates a viable/useable product that reaches potency and flavor preferences, which requires the accurate compounding of known inputs in the formulation. And to accurately compound a formulation, the contents of the compounds being used must be known. As such, many people involved in creating medicine today are not experienced (novice) in the art, nor are they yet required to be held accountable for the qualities of their formulations. Streamlining and providing quality control to these processes is increasingly important.

From a pharmaceutical (cannabis) perspective, educational and operational solutions could greatly benefit those tasked with understanding and creating the different potential formulations and devices used in aerosol delivery to patients prescribed cannabinoid-based medications. Given the inevitable level of trial and error associated with this budding form of medicine, practiced by many not trained in pharmaceutical compounding, solutions that enable efficient reliability of various (known) inputs used in the creation of inhalable cannabinoid solutions is increasingly important.

Critically, the producer benefits from knowing the properties of the cannabinoid extract(s) being used in a particular formulation, such potency and level of refinement (winterized vs unwinterized) and the target properties of the formulation.

Assuming the producer has the extract, he must source inputs (additive(s) and cartridges/battery) for creating and delivering a viable formulation from said extract. Generally producers purchase large amounts of inputs to develop their target formula and cartridge combination(s), and may use automated technology to create large production runs. As more patients/users require more formats of cannabinoid-based medicine, the complexity of creating different solutions increases for producers. This decreases the efficiency of the producer, who has to do more testing (trial and error) for increased variation, more time ordering different inputs, and has an increased risk of error in terms of creating a targeted formulation if the inputs for different formulations and patients mix during production. As mentioned, if there are multiple extracts or multiple finished formulations being used, the complexity for the producer increases.

As such pharmacists/medical providers and patients also need inventory management solutions that allow them to efficiently source the inputs and components need to achieve varying levels of production ('unit-of-use'). While some producers may need optimized kits for testing for larger production runs, some patients or other end users would benefit from 'unit-of-use' inventory systems for formulating and delivering their own medicine.

Maintaining inventories for inputs (cartridges, carrier/diluent/flavorant) and the requisite tools for filled cartridge production can be challenging, as they're sourced from independent manufacturers and generally have minimum order requirements. This requires a lot of time and unnecessary expense, especially when new formulations are tested and produced. The inability to source cartridge and diluent/carrier/flavorants (herein referred to primarily as 'additives') necessary to achieve a predefined level of production is especially challenging for those trying to test products or do small production runs for patients or for personal use.

Traditionally, pharmacists are trained to do consultations, record keeping for controlled substances, and keeping of accurate inventories. There is a need for tools that help the dispensing of cannabis products become more pharmaceutical as traditional pharmacy, as many cannabis pharmacists were not trained in pharmacy and are not employed by organizations that have resources to enable comprehensive product and service offerings.

For a variety of reasons, many individuals go outside of the pharmaceutical and traditional medical channels to consume similar medicinal cannabis-derived compounds. In many states, even medical use is prohibited, and recreational use can result in jail time. Therefore, many consumers and 'self-described' patients are turning to black markets to source prefilled inhalable devices as well as the components and inputs to make them. The role of the black market in the cannabis supply chain is well known by those skilled in the art. In many states, even medical cannabis market participants (patients and caregivers) are sourcing their medicine through unregulated sources. While regulation is catching up, it's slow moving.

The proliferations of the black market have several undesired externalities. Many cartridges in the market today are known to have false labeling regarding potency and ingredients; numerous popular vape products have been found to contain toxic, tainted ingredients and false labeling in the market today. Filled cartridges in certain markets are known to be drastically overpriced: lack of supply in many markets has driven the price of THC/CBD e-liquid filled cartridges to exceed 1000% of manufacturer's cost. These realities of the current market for inhalable formulations of cannabis compounds warrant solutions that will bring quality-controlled, cost-effective, verifiable products to market for both recreational and medicinal users.

As such, there is a need for a solution that provides accurate, corresponding labeling for inhalable formulations (as well as other products) in the rapidly growing and fast changing cannabis industry. It's well known to those skilled in the art that mislabeling of products, particularly cartridges for use in aerosol delivery devices, containing formulas with medicinal compounds. To add, these formulations are not being created by pharmacists or chemists, but people producing largely black market/rec products, who, in many cases, label their products as having defined medicinal properties. Even in non-medical use cases, it would be greatly beneficial to a consumer to be able to create their own known formulations from a known cannabis-based extract. In medical use cases, it's absolutely critical that labeling is sounds to achieve a desired/prescribed dose. In medical use cases, labeling and packaging requirements are already being mandated by states, and the need to keep up to date with these regulations and labeling requirements is critically important to the producer of cartridges. Solutions that enable custom labeling at relatively low levels production levels are important as it may be prohibitively expensive/time consuming for the producer to invest in those resources.

In addition to cost and labeling and safety issues, filled cartridges are marketed/sold to consumers as disposable, despite the fact that (some) cartridges are refillable, leading to significant waste. There is a need for a solution that enables the personal filling and refilling of cartridges from a inhalable formulation. Most inhalable formulations on the market today are sold as pre-filled, disposable cartridges. This leads to waste and unnecessary product degradation and failure. The longer a formulation sits in a cartridge without being used, the more it degrades. Additionally, without a ready supply (container) of inhalable formulation and a tool to draw and dispense it, the concept of refilling for the individual/personal use end users is not viable. Cartridge technology will continue to improve and become more refillable. Cartridges, despite the fact that many can be viably filled multiple times before being discarded, are generally disposed of after single use.

While certain factors impact the a 'refillability' of a cartridge—particularly the construction/materials of the cartridge and the properties of the formula being housed in it and vaporized. For example, a formulation made with an amount of highly refined extract, like pure THC distillate, and an amount of diluent, will vaporize 'cleaner' than a formulation made with the same amount of crude THC extract and diluent. The impurities in the crude solution, if it even if the solution homogenizes to a liquid formula suitable for use in the cartridge, will generally clog the atomizer and other parts of the cartridge at a faster rate than the cartridge containing the refined extract solution.

There is a need for a filling/refilling kit that contains empty cartridges, a predefined amount of a ready-to-vape formulation, and a draw/dispensing tool (i.e. syringe). This is optimized for refilling (waste reduction) and to reduce the chance of cartridge/formula degradation, which can take place when the formulation sits in the cartridge for an extended period of time.

Inhalable Formulations

Medicinal formulations (for use in an aerosol device) are made from concentrated forms (pure or with a solvent) of medicinal compounds (may be referred to as 'extracts' or 'concentrates' herein). The process of creating formulations typically involves diluting medicinal extract (i.e. cannabinoid extract), by combining it with an amount of carrier mixture (diluent) in a container, heating (to ~150 F), and stirring the mixture until it reaches a homogeneous state with desired properties, at which time it can be injected into a cartridge for use in an aerosol device. Those skilled in the art know that a variety of heating methods can be utilized in the mixing process, such as a hot plate, microwave, or placing a container in hot water. Other additives (such as terpenes) may be added to adjust flavor and properties of the formulation to enable atomization of the formula in the aerosol device.

There are a range of medicinal extracts used in the production of inhalable formulations, many of which of have different properties which require different amounts/types of carriers/diluents (herein referred to primarily as 'additives') to achieve a suitable formulation for use in a cartridge. In general diluents and carrier liquids both act as solvents/emulsifiers/homogenizers/liquidizers/thickening and stabilizing agents, to create a suitable formulation. Traditionally, formulations used in aerosol devices have contained the active/organic compound nicotine (in concentrated form) and a carrier base generally consisting of propylene glycol (PG), glycerol (VG), or PEG-400, or some combination thereof, and flavoring solution(s).

More recently, inhalable formulations are being created to enable the consumption of the medicinal compounds other than nicotine. For example, formulations containing cannabis extracts, and their active ingredients THC and CBD, are increasingly popular. Medicinal compounds/extracts according to the present invention can have varying properties, which have led to the development of new recipes to enable inhalable formulations in an aerosol device. More frequently, in cannabis derived formulations, for example, non-traditional carrier base/diluents and flavorants (and their corresponding ratios) are being used (different than those used in nicotine e-cigarette formulations).

For example, different combinations and types of carriers/diluents and flavorants used in formulations derived from different kinds of cannabis extracts:

Carrier/Diluent:

In general, carriers, which are used to 'carry' cannabis compounds/extracts, are used in larger ratios when the extract cannot be easily diluted. Some cannabis extracts contain varying amounts of lipids and waxes and other plant constituents which are not oil soluble and may separate or cloud the final product. Unwinterized extracts include BHO and Rosin. When using unwinterized extracts, with high lips/waxes content, it is believed by many skilled in the art, that it is generally better/necessary to use a carrier (base). Typically, these are MCT, PG, and PEG. Diluents dissolve into the extract and thin it, allowing less additives than when using carrier (base). Diluents dissolve into your extract and force separation of non-soluable components. Flavorless terpenes and other solutions, like triethyl citrate, are currently being used as diluents. Diluents, it is believed by many skilled in the art, are optimal for winterized cannabis extracts, meaning those which have had the majority of the lipids (fats) and waxes removed. Generally winterized extracts include distillate and post processed (finished/polished) CO2. There are a large variety of MCT oils (9 variations?) that are potentially suitable for use as a diluent.

Flavorant:

non-traditional flavorants such as terpenes, or combination of terpenes, are being used increasingly in inhalable formulations derived from cannabis extracts, particularly those derived from refined cannabis extracts where much of the natural flavor is stripped out during the extraction process.

As highlighted, the extracts used in the production of inhalable formulas may have varying properties which are determined largely by the extraction method used to produced them. Compared to less refined extracts like BHO (unwinterized), more refined extracts like distillate (winterized) have a higher purity/potency and they contain less organic compounds, such as fats/lipids/waxes and plant matter. Ultra-refined cannabis THC extracts can exceed 90% potency. Additionally, a single extract can be adapted to have different properties. It is known to those skilled in the art that 'decarbing', a method of heating an unwinterized extract to change its properties, can be used to decrease the viscosity of non-winterized cannabis extracts. Decarbing effectively volatizes compounds in the extract, such as terpenes, which lessens viscosity.

Indeed, Unwinterized Extract A, Decarbed Extract A, and Distillate made from Extract A may all be used to create inhalable formulations but will have different fundamental properties (and require different formula inputs) that will result in fundamentally different vaping experiences (flavor, dose/inhale, leaking/clogging) in a given aerosol delivery device.

Cartridges

Cartridges in the present invention are designed to be compatible and/or adaptable for use with range of pharmaceutical compounds or synthetic compounds which are capable of being vaporized (or volatilized) at a relatively low temperature and without harmful degradation products. These include menthol, caffeine, taurine, THC and nicotine. These cartridges can also be adapted. The capillary wick may have any suitable capillarity and porosity so as to be used with different liquid physical properties such as density, viscosity, surface tension and vapor pressure.

Cartridges according to the present invention can take a variety of shapes and sizes, colors, and styles. They are typically cylindrical but may be 'pods' or another non-cylindrical format.

E-liquid is vaporized and inhaled via a PV, which has three fundamental parts: an e-liquid storage components, which generally includes a mouthpiece, an atomizer which serves as the heating element responsible for vaporizing the liquid into an inhalable mist, and a battery unit that serves as the power supply in PV systems. A 'cartridge' or 'cartomizer' or 'clearomizer' option has been developed for PV systems that brings the separate reservoir and atomizer component together in a single integrated component.

The focus of this invention consists of detachable cartridges (atomizer and liquid reservoir) and power sources. These cartridges can be disposable, but are provided with lids to be refillable. Cartridges are generally cylindrical, but can take other shapes; one popular version of non-cylindrical cartridge being used today is the 'pod'. Indeed, the size, shape, design, and material(s) of a cartridge can impact its functionality and durability.

Similarly, aerosol delivery devices of the present invention have been developed with unique properties and constructions that can produce different Vaping experiences' of the same inhalable formulation. For example, the reservoir portion of an aerosol delivery device can be configured to retain and enable transfer of a unique formulation to the wick, which can be made from material adaptable to facilitate transport of the unique formulation (usually a liquid) from the reservoir to the heating chamber, via capillary action for example. Cartridges containing only ceramic coils (no wick) or large (2.0 mm for example) inlet holes, which allow the passage of an inhalable formula to travel to the heating element, are known to be more optimal for more viscous formulations.

Cartridges, particularly the atomizer portion, have unique properties and structures that can be optimized for delivering e-liquids with varying physical properties, such as viscosity, density, surface tension, and vapor pressure. One cartridge according to the present invention has an adaptation which ensures that the wick is always wet in the heating area, preventing overheating, which can lead to thermal degradation of e-liquid and its core compounds.

Variations in a cartridge's structure affect airflow speed and direction, vapor particle size (i.e. 5 micrometers ($\mu$m)), e-liquid coloration, e-liquid holding volume, and battery connectivity. Cartridges are constructed from a variety of materials with different levels of durability. Many are intended to be disposable after a single use. Indeed, different cartridges of the present invention are optimized for different kinds of e-liquids.

Cartilage Filling

The filling process can vary for different cartridges and liquids. Cartridges have different constructions and assemblies, which require specific filling protocols to maximize the use of the cartridge. One of the goals of the present invention is to facilitate ease of this filing process for a variety of different filing protocols.

Some cartridges must be kept upright during the filling process. The viscosity of e-liquid can also impact the optimal filling methodology. For example, some cartridges especially those with higher viscosity e-liquids may require a longer period of time to soak into the atomizer before it can be used in a PV system. The present inventive method and device seeks to overcome the challenges associated with hand filling methods, which are not addressed by automated cartridge filling technology which is expensive and inefficient for personalized formulations.

In general filling methodologies may change based on cartridge type and e-liquid type. E-liquid cartridges are generally optimized for certain levels of battery power. PV batteries are ubiquitous, rechargeable, and adapt to the vast majority of cartridges via a 510 thread. Certain power levels will align with certain heating elements to produce an optimal vaping experience. Many batteries made today have variable voltage functions, allowing an end user to vape optimally across different cartridge types.

Medicinal Cannabis

Cannabis extracts have varying medicinal benefits. It is an oil-based whole plant product that contains inactive and active compounds contained in the cannabis plant such as cannabinoids, terpenes and/or flavonoids. The extracts and/or delivery methods described allows a wide range of prevention, treatment and management options for patients. Some compositions are a mixture of 20 flavonoid compounds which are well known as antioxidants and which also scavenge damaging free radicals. Another terpene-based compositions relate to enriched formulations that are biomimetic to the aroma, flavor, and pharmaceutical effect of various biochemicals naturally present in particular strains of the Cannabis plant, including terpenes and cannabinoids.

In one aspect, some embodiments disclosed therein related to methods of making a composition for imparting one or more desired effects to a subject. The method includes preparing a composition in which a plurality of chemical compounds which are known to occur in a cannabis strain and are associated with at least one desired effect in a subject are enriched, wherein the amounts or levels of the plurality of chemical compounds with respect to one another in the composition are about the amounts or levels of the plurality of chemical compounds with respect to one another in the cannabis strain.

Implementations of embodiments of the method according to this aspect and other aspects of the present disclosure can include one or more of the following features. In some embodiments, the preparation of the composition includes (i) obtaining a first enriched or purified composition of a first chemical compound from among the plurality of chemical compounds associated with at least one desired effect in a subject and which is known to occur in a cannabis strain, and (ii) combining the first enriched or purified composition with a second enriched or purified composition of a second chemical compound from among the plurality of chemical compounds associated with at least one desired effect in a subject and which is known to occur in the cannabis strain. In some embodiments, the plurality of chemical compounds are selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements. In some embodiments, the plurality of chemical compounds includes at least one terpene compound selected from the group consisting of monoterpenes, diterpenes, triterpenes, hemiterpenes, sesquiterpenes, sesterterpenes, sesquiterpenes, and notisoprenoids.

In some embodiments, the plurality of chemical compounds includes at least one terpene compound selected from the group consisting of 3-carene, a-bisabolol, $\beta$-caryophyllene, bisabolol, borneol, camphene, carene, caryophyllene, caryophyllene oxide, citronellol, eucalyptol, fenchol, geraniol, $\gamma$-terpinene, guaiol, humulene, isopulegol, limonene, linalool, menthol, myrcene, ocimene, p-cymene, phellandrene, phytol, a-pinene, $\beta$-pinene, terpenolene, terpinene, terpineol, and valencene. In some embodiments, the plurality of chemical compounds includes at least one terpene compound selected from the group consisting of caryophyllene, limonene, linalool, myrcene, a-pinene, and $\beta$-pinene.

Some of the medical benefits attributable to one or more of the cannabinoids isolated from cannabis include treatment of pain, nausea, AIDS-related weight loss and wasting, multiple sclerosis, allergies, infection, depression, migraine, bipolar disorders, hypertension, post-stroke neuroprotection, epilepsy, fibromyalgia, as well as inhibition of tumor growth, angiogenesis, and metastasis. Studies have shown that cannabinoids may also be useful for treating conditions, such as glaucoma, Parkinson's disease, Huntington's disease, migraines, inflammation, Crohn's disease, dystonia, rheumatoid arthritis, emesis due to chemotherapy, inflammatory bowel disease, atherosclerosis, posttraumatic stress disorder, cardiac reperfusion injury, prostate carcinoma, and Alzheimer's disease.

Terpenes are compounds that are produced by cannabis. Reportedly, as many as 200 or more terpenes can be produced by cannabis plants, although the types and ratios of terpenes produced by a cannabis strain are dependent on genetics and growth conditions (e.g., lighting, fertilization, soil, watering frequency/amount, humidity, carbon dioxide concentration, and the like), as well as age, maturation, and time of day. Terpenes have been shown to have medicinal properties and may be responsible for at least a portion of the medicinal value of cannabis.

Some of the medical benefits attributable to one or more of the terpenes isolated from cannabis include treatment of sleep disorders, psychosis, anxiety, epilepsy and seizures, pain, microbial infections (fungal, bacterial, etc.), cancer, inflammation, spasms, gastric reflux, depression, and asthma. Some terpenes have been shown to: lower the resistance across the blood-brain barrier, act on cannabinoid receptors and other neuronal receptors, stimulate the immune system, and/or suppress appetite.

Due to the wide variety of benefits, there is a growing need for the ability to personalize treatment, and to provide devices and methods capable of facilitating personalized treatment on a growing scale. Ultimately, these devices may be provided whole sale with guidelines to provide personalized treatment based in specific factors listed above and discussed in greater detail below.

'Unit-of-Use Kits'

The invention, in part, stems from the realization that there exists a need for a convenient method for preparing and delivering accurate, controlled, and/or predefined amounts of selected cannabinoid formulations, for medicinal purpose. Such a method would add tremendous efficiency to many pharmacists, patients, or anyone tasked with delivering a prescribed unit medicinal dose of an amount of one or more medical cannabis compounds via aerosol device. It would require a reduction in required inventory/inventory management and enable more accurate formulations. In a pharmaceutical context, the invention, results in an increased availability of medicine to patients that formula is true to what was prescribed or what's desired. This invention would also enable an accurate/dependable patient/medicine-specific labeling solution, solving a major pain point and reducing a major risk faced by the industry today.

From a patient's perspective (whether prescribed my medical professional; or themselves/recreationally), the ability to create and deliver targeted medicinal treatment without having to wait for a pharmacist, resort to the black market to source or alternate methods of ingesting the core medicinal compounds (smoking, edibles), cost savings, potential reduction of waste may all provide different levels of utility. The invention provides methods/kits that enable the preparation of unique inhalable cannabis formulations, as well as methods for their use. There is also a need for pharmaceutical formulations comprising known concentrations, or known relative concentrations, of medicinal cannabis compounds for use with said delivery devices. Various aspects disclosed herein may fulfill one or more of these needs.

The systems and methods described herein each have several aspects, no single one of which is solely responsible for its desirable attributes. Without limiting the scope of this disclosure as expressed by the claims that follow, the more prominent features will now be discussed briefly. After considering this discussion, and particularly after reading the section entitled "Detailed Description," one will understand how the sample features described herein provide for improved systems, devices, compositions, and methods for" delivering medicinal cannabis compounds to a patient.

Method 1—Compounding Specific Formulations

In accordance with a first aspect of the present invention, there is provided a method for manufacturing filled cartridges (producing e-liquid and filling cartridges for use in a PV). The method includes the steps of providing a kit that includes an enclosure and components, materials (aerosol precursors; additives), and methods (instructions) for creating a predetermined amount of a pharmaceutical formulation (a compounded pharmaceutical formulation) using at least one cannabis (cannabinoid) compound. The method includes providing pre-measured amounts of active (cannabinoid) and inactive (e.g., base; diluent; additive) agents for the preparation and filling of single or multiple prescriptions (formulations) which may consist of a predetermined amount of formulation inputs (cannabinoid extract, additives) and a predetermined amount of cartridges (aerosol delivery device components which store and enable inhalation of said formulations), and are thus referred to as 'unit-of-use' kits. It includes the step of providing an optimized filling station/apparatus and enclosure that holds components for convenient use and transportation. Optionally, the method may include providing packaging and labeling that is specific to the medicinal formulation(s) (which may come applied or have to be applied by the end user), placing tools and components back into the kit, storing unused liquid in an empty container, closing the kit, and reusing the kit to fill additional cartridges or refill cartridges previously filled using the kit.

In some embodiments, the medicinal cannabis compound provided in the kit contains a known amount of one or more cannabinoids. In some such embodiments, the one or more cannabinoids have a ratio of CBD to THC of between 1:1 and 1:100.

In some embodiments, the method involves sourcing an amount of extract containing medicinal (cannabinoid compounds) from a testing facility or related entity-type, where the potency has been verified by an accredited third-party testing entity. The method may include the testing lab (kit provider) provides product-specific labeling that can be applied to the products and may be required by regulation or at the request of the end user sourcing the kit.

In some embodiments, the kit may contain a plurality of known (tested) extracts and/or a plurality of mixing containers, so the end user can create and use a unique formulations from each of said plurality of extracts (containing a known amount of medicinal compound; cannabinoids for example). In these embodiments, the kits are preferably designed by the kit provider. In some embodiments, the kit contains at least one mixing element, an additive (inactive or active) agent stored in a container. The kit may also contain a second additive, housed in a second container and preferably not the same type/amount additive that is in the first container. Both the first and second containers preferably contain an active or inactive compound selected from the group consisting of cannabinoids, terpenes, mct oils, PG/VG, or other known additives or other commonly used additives in cannabinoid formulations for use in aerosol delivery devices, which are listed in the prior art section.

One aspect of an embodiment of the current invention is that the active and inactive/active agents are physically mixed by a pharmacist to produce a compounded pharmaceutical composition. It is intended that the compounded compositions and the compounding methods of the invention be performed by either a qualified pharmacist or a qualified physician. Thus, as used herein, when reference is made to a pharmacist, a pharmacist and a physician are intended.

Kit 1—Compounding Predefined Formulations Using Known Inputs

One aspect of the disclosure relates to a kit that enables the creation of specific formulations of compounds suitable for delivery via vaporizations (an aerosol delivery device). In various embodiments, the kit contains inputs needed to make a target formulation containing a known amount of medicinal compounds from cannabis extract (cannabinoids), to be combined with at least one aerosol precursor included in the kit, to create a predetermined medicinal formulation or formulation(s) for use in an aerosol delivery device.

The aerosol precursor(s) included in the kit could be a variety of organic compounds and could also have medicinal properties (i.e. terpenes). The kit includes at least one mixing container, which may contain the known amount of extract, for combining the included additive(s) (organic compound(s)) with the known amount of active compound (cannabis extract), enabling the creation of a targeted formulation to deliver specific dose and effects. The mixing container can optionally be used for storage of the single formulation created using the kit. The kit may also include tools, such a syringe/filling tool, mixing tool, or a heating device, to aid in the recommended processes of creating the predefined formulation and filling the unique cartridges included in the kit. Kits may include kit-specific instructions with information about creating the specific formulation, mixing, and filling/priming the specific cartridge component for use, which battery power/voltage to use with the unique filled cartridges produced using the kit, as well as a full list of kit contents, or producer branding/logos. and priming them for use in an aerosol device. The kit may optionally contain custom (white labeled) labeling and packaging, which may contain information regarding the product and/or the supplier and/or the patient, as required under regulation/compliance requirements, for the products' end user.

The kit may include packaging with labels applied, or with labels that must be applied by the user of the kit. Kits may include solutions for cleaning cartridges during filling or after use, which may better enable refilling of cartridges after use. The kit may also contain a variable battery suitable use for the cartridges in the kit and/or recommend power/battery/voltage devices to use to power the specific model of cartridge containing a unique formulation.

In some embodiments, the medicinal cannabis compound provided in the kit contains a known amount of one or more cannabinoids. In some such embodiments, the one or more cannabinoids have a ratio of CBD to THC of between about 1:1 and about 1:100. In some embodiments, the method involves sourcing an amount of extract containing medicinal (cannabinoid compounds) from a testing facility or related entity-type, where the potency has been verified by an accredited third-party testing entity. The method may include the testing lab (kit provider) provides product-specific labeling that can be applied to the products and may be required by regulation or at the request of the end user sourcing the kit.

In some embodiments, the kit contains at least one mixing element, an additive (inactive or active) agent. The kit may contain a plurality of additives, housed in a plurality of containers and preferably not the same type/amount additive that is in the first container. Both the first and second containers preferably contain an active or inactive compound selected from the group consisting of cannabinoids, terpenes, mct oils, PG/VG, or other known additives or other commonly used additives in cannabinoid formulations for use in aerosol delivery devices, which are listed in the prior art section.

One aspect of an embodiment of the current invention is that the formula inputs (combination of active and inactive/active agents) are physically mixed by a trained pharmacist to produce a compounded pharmaceutical composition. It is intended that the compounded compositions and the compounding methods of the invention be performed by either a qualified pharmacist or a qualified physician.

In some embodiments, the kit may contain a plurality of known extracts (amounts and concentrations of medicinal compounds) and/or a plurality of mixing containers, so the end user can create multiple targeted formulations under this method/kit format. In some embodiments, the kit may contain tools, such as a heating tool, stirring rod, and spill wipes.

Method 2—Select And Store Different Ratios

In accordance with another aspect of the present invention, there is provided a method for manufacturing filled cartridges (creating inhalable formulations and filling cartridges for use in a vaporizer). The method includes the steps of providing a kit that includes an enclosure and components (cartridges), materials (at least one aerosol precursors), and methods (instructions) which will enable a variety of formulations from (unknown) medicinal (cannabis) extracts, filling cartridges using the various formulations of the kit. The method includes providing a predetermined amount of at least one aerosol precursor (additive) and a plurality of empty cartridges (aerosol delivery device components which store and enable inhalation of said formulations) and are thus may also be referred to as 'unit-of-use' kits. The method also includes the step of providing an optimized filling station/apparatus and enclosure that holds components of the kit for convenient use and safe transit. The method also includes filling cartridges or a range of cartilage models with at least one inhalable formulation. Optionally, the method may include providing packaging and labeling for application onto supplemental packaging, placing tools and components back into the kit, storing unused liquid in an empty container, closing the kit, and reusing the kit to fill additional cartridges or refill cartridges previously filled using the kit.

In one embodiment, the method enables a kit containing multiple models of cartridges.

In one embodiment, the method enables a kit containing at least one mixing element, an additive (inactive or active) agent, selected from the group consisting of cannabinoids, terpenes, mct oils, PG/VG, or other known additives or other commonly used additives in cannabinoid formulations for use in aerosol delivery devices, which are listed in the prior art section.

In other embodiments, the kit may also contain a second additive, housed in a second container and preferably not the same type/amount additive that is in the first container. Both the first and second containers preferably contain an active or inactive compound (additive) selected from the group consisting of cannabinoids, terpenes, mct oils, PG/VG, or other known additives or other commonly used additives in cannabinoid formulations for use in aerosol delivery devices, which are listed in the prior art section.

The kit contains predetermined labeling as determined by the designer. The labeling may be on stickers/labels or engraved/printed onto components pieces.

Kit 2—Compounding Various Formulations From Unknown Extracts

One aspect of the disclosure relates to a kit that enables the creation of formulation of compounds suitable for delivery via vaporizations (an aerosol delivery device). In various embodiments, the kit contains inputs needed to make a target formulation with an unknown (to the kit provider) amount of cannabis extract, to be combined with at least one aerosol precursor included in the kit, to create a formulation or formulation(s) for use in an aerosol delivery device. The aerosol precursor(s) included in the kit could be a variety of organic compounds and could also have medicinal properties (i.e. terpenes).

The kit includes a plurality of mixing containers for combining the included additive(s) (organic compound(s)) with an unknown amount of an active compound (cannabis extract), enabling the testing and sampling of different ratios of said extract:additive(s). The mixing container can optionally be used for storage of a formulation created using the kit. The kit may also include tools, such a syringe/filling tool, mixing tool, or a heating device, to aid in the recommended processes of creating the predefined formulation and filling the unique cartridges included in the kit. Kits may include kit-specific instructions with information about creating specific formulations, mixing, and filling/priming specific cartridges for use, which battery power/voltage to use with the unique filled cartridges produced using the kit, as well as a full list of kit contents, or producer branding/logos. and priming them for use in an aerosol device.

The kit may optionally contain custom (white labeled) labeling and packaging, which may contain information regarding the product and/or the supplier and/or regulatory and compliance the filled cartridges and applying labels with unique information. Kits may include solutions for cleaning cartridges during filling or after use, which may better enable refilling of cartridges after use. The kit may also contain a variable battery suitable use for the cartridges in the kit and/or recommend power/battery/voltage devices to use to power the specific model of cartridge containing a unique formulation.

The kit contains at least one mixing element, an additive (inactive or active) agent. The kit may also contain a second additive, housed in a second container and preferably not the same type/amount additive that is in the first container. Both the first and second containers preferably contain an active or inactive compound selected from the group consisting of cannabinoids, terpenes, mct oils, PG/VG, or other known additives or other commonly used additives in cannabinoid formulations for use in aerosol delivery devices, which are listed in the prior art section.

Optionally/in some embodiments the kit (or any variations highlighted above) does not include any cannabinoid extract or compounds.

In some embodiments, the kit also contains at least one empty container for storage of a unique formulation.

Method 3—Refilling Cartridges with Pre-Formulated Formulations

In accordance with another aspect of the present invention, there is provided an end user the means a cartridge refilling option. The method includes the steps of providing a kit that includes an amount of empty cartridges, a container containing a predetermined amount of an inhalable formulation containing a known amount of a medicinal compound. The method may also include providing tools for use of the kit, instructions, and cleaning solutions. The method includes providing an amount of the inhalable formulation exceeds the total capacity of the empty cartridges included in the kit. i.e. 2.0 ml of extract for a kit with 2 empty 0.5 ml cartridges. In some embodiments, the kit contains an optimized filling station/apparatus and enclosure (box). The method may also include packaging and labeling, which could include medicinal information, producer info, etc.

In some embodiments, the medicinal cannabis compound provided in the kit contains a known amount of one or more cannabinoids. In some such embodiments, the one or more cannabinoids have a ratio of CBD to THC of between about 1:1 and about 1:100.

In some embodiments, the kit contains an amount of extract containing medicinal (cannabinoid compounds) that has been tested at a verified third-party, accredited testing entity. In some embodiments, the testing lab provides product-specific labeling (possibly as the kit provider) that can be applied to the products and may be required by regulation or at the request of the end user sourcing the kit.

In some embodiments, a mixture of the known medicinal active agent and at least one additive (inactive or active) agent is used in the compounded pharmaceutical formulation, where the additive is selected from the group consisting of cannabinoids, terpenes, mct oils, PG/VG, or other known additives listed in the prior art section above.

Kit 3—Refilling Kit

In another embodiment, a version of the kit includes a number of empty cartridges and a predetermined amount of an inhalable formulations containing medicinal compounds. More specifically, this version of the kit may contain more formulation than the total volume of the cartridges included in the kit. In some embodiments, a cannabis oil extract having a known amount refers to a cannabis oil extract having a known concentration of one or more medicinal cannabis compounds; in other embodiments, a cannabis oil extract having a known amount refers to a cannabis oil extract having a known relative concentration (i.e., a known ratio) of two or more medicinal cannabis compounds. In some embodiments, the inhalable formulation included contains an amount of one or more cannabinoids. In some such embodiments, the one or more cannabinoids have a ratio of CBD to THC of between about 1:1 and about 1:100. In other embodiments, the one or more.

In some embodiments, the kit contains an amount of extract containing medicinal (cannabinoid compounds) that has been tested at a verified third-party, accredited testing entity. In some embodiments, the testing lab provides product-specific labeling (possibly as the kit provider) that is/can be applied to the products and may be required by regulation or at the request of the end user sourcing the kit. In some embodiments, a mixture of the known medicinal active agent and at least one additive (inactive or active) agent is used in the compounded pharmaceutical formulation, where the additive is selected from the group consisting of cannabinoids, terpenes, mct oils, PG/VG, or other known additives listed in the prior art section above.

Apparatus—Filling Station

It is another aspect of the invention to provide a filling station/apparatus for each kit. Each kit is compactly packaged, incorporating an apparatus (fill station) having individual recesses or receptacles for each component in the kit, with each such recess being uniquely shaped or dimensioned to receive only its designated item(s). The tray presents the components and materials in a way that minimizes the time and effort of the end user to follow the instructions and complete the production sequence as described in the instructions. In other words, components are positioned to require minimum movement/travel while performing the processes of creating different forms of e-liquid and/or filling and sealing unique cartridges for that e-liquid. Moreover, the instructions included in kits may be adapted to clearly outline which components are which and where the sit in the tray/apparatus, reducing any confusion for the end user. The apparatus is designed to fit inside a box that is durable and has interior clearance for any components rising above the surface level of the apparatus, such as the bottoms of the cartridges. The apparatus can be removed from the box and stand on its own.

Custom Instructions and Labeling

It is another aspect of the present invention to provide tailored 'unit-of-use' style instructions/methods in the kits. These instructions may contain unique information relating to the unique amounts and types of inputs in a specific kit. I.e. kits adapted to create different amounts of formulation (in kit 1, for example) and offering a particular model/number of cartridges will have instructions tailored to those inputs and related processes, to be completed by the kit provider. Instructions and methodologies are displayed in the form of an instructional manual, which may be found printed inside the box/container of the kit, under the lid for example, or in a separate document/pamphlet included in the kit, or digitally, to be accessed by the user via a technological device such as a computer or smartphone. The information described/covered under the current invention is arranged and the instructions prepared in a manner that assures that someone of novice skill in the art could complete use the kit successfully. As mentioned, in some embodiments, the instructions are adapted for use of a specific kit or input included in the unique kit and contain unique information compared with other kits. The instructions may convey particular procedures, which instruments and materials (and the exact amounts) provided in the kit are used, including the processes highlighted in the methods of the above sections. In some embodiments, the instructions may also highlight the shape and positioning of each component, as each sits in the kit, as well as how they should be positioned when enacting the methods included in the kits, to reduce end user confusion and likelihood of error.

In certain embodiments, the kit includes adapted labeling solutions to be applied to the box/enclosure unit, and components and packaging provided in the kit(s). The labeling may include generic information and enable the end user to adapt the labels, or may contain specific, predetermined labeling. The medicinal/pharmaceutical market particularly could benefit from solutions that provide accurate labeling (for consumers), cost-effectively (especially for smaller producers that might resort to generic, misleading labels given the cost-structure behind creating custom labels).

In general, the kit(s) in the present invention enable a process of defining an inhalable formulation is consolidated with purchasing inputs for a desired amount of said formulation. As such, practitioner inventory costs are reduced, formulas become more accurate, product quality increases overall, and, critically, medicinal outcomes (produced by provider) become more predictable and recreational users (self-medicating) have a much better option than purchasing filled cartridges (medicine; highly likely is mislabeled) on the black market. The present invention serves to enable producers of all sizes and ambitions, and all extracts, to sample and test different formulation combinations without having to incur major costs or operational/mechanical pitfalls (especially for novice users; such a trial and error defined process is known to by those skilled in the art today).

Kits (their inputs) can be defined by either a cartridge filler (producer) or a kit provider (collectively herein called 'kit designers'). Principally, the cartridge model and inhalable formulation inputs can be defined by either the kit provider or the end user. The kit, at the designer's discretion, may also include components/tools, packaging/labeling, and cleaning materials. Each kit can, in terms of the volume of formulation inputs (additives; or extract and additives) and total cartridge (unit capacity and total number), be customized for producing a predefined amount of an inhalable formulation, as well a target strength and level of vapor production (preferences: dosing and taste/flavor), for a given amount of extract from a specific aerosol generating device (cartridge battery combination). As such, the kit designer (producer, patient or kit provider) may also desire to provide specific labeling for the produced units, including logos, certain information, dosing instructions, etc. The kit designer might also need request a certain style of input, such as packaging or labeling, for performance or regulatory/compliance reasons.

In general, kits maybe offered/created based on a desired number of 'fills' (total liquid in recommended formula/single unit cartridge capacity—i.e. 4.0 ml/0.5 ml=8 fills) specifically to enable an adaptable (unit-of-use) refill system. These unit-of-use kits also come with tailored instructions or the particular amount of formulation and number of cartridges being filled in the unique kit. End users and providers of inputs, and providers of filled (disposable) cartridges will all be able to find value from the present invention. The kit may also recommend power/battery/voltage devices to use to power the specific model of cartridge containing a unique e-liquid.

The components needed in filled vape cartridge production generally include empty cartridges, inputs (additives) for an inhalable formulation to be created from a given amount of extract, which generally contains some amount of medicinal compounds and has unique properties as compared to many other extracts with the same medicinal compounds. A power source (generally a 510 thread battery; ideally variable voltage to achieve different outcomes with different cartridge/formulation combinations), mixing tool, syringe tool (draw and dispense formulas when in liquid state) filling tools, containers, a heat source (myriad available known to those skilled in the art), some semblance of instructions (generally has to be pulled from the web), some control or filling tool or mechanism to hold cartridges (for larger scale production) and cleaning and packaging solutions.

Importantly, cartridges and formulations must have properties that sync with each other (must be relatively optimized for each other—i.e. in the present embodiment shows different combinations of cartridges and formulations) to provide an optimal or close-to-optimal vaping experience. Given the range of medicinal extracts being used (particularly cannabinoid-based) to create formulations, there is a wide range of cartridge-formulation-additive combinations that may produce a particular outcome (whether medicinal or recreational), under a given amount of power (lesser consideration but still does impact the outcome of the particular cartridge-formulation combination, as each combination may have an optimal temperature or temperature range, enabled by a particular voltage. As the use of cannabinoid and other medicinal compounds increases, solutions that control quality and dosage, in a way that provides safe and medicinal benefits through vaping products is increasingly important. The focus of this invention.

As discussed above, currently cartridge producers are sourcing inputs from myriad producers, in myriad markets, with little regulatory oversight on said inputs (cannabis market). This is particularly the case for smaller scale producers and personal providers who use their own sourced extracts (containing largely unknown cannabinoid compounds). It is not advisable or efficient to hold large inventories of cartridges and other inputs that are only optimized for certain extracts/formulations. A testing/sampling solution for these user types is need. And if these producers ever want to produce medicinal, prescription products, they will demand/need a solution that enables verified testing of the extract, and resources that provide specific recipes/procedures to accurately compound the necessary inputs to create such medicinal formulations.

For this reason, corresponding labeling will be increasingly important for medicinal and consumer participation, as the premium for legitimate end products that serve consumers/end users honestly and efficiently will be continually important. Thus, by establishing a kit provider that can inventory the inputs, (and can potentially test and certify the medicinal extracts/compounds that would be used in kit formulations), inventory management for many practitioners is greatly streamlined The kit provider also provides other efficiencies, highlighted in the accompanying embodiments. A custom apparatus that holds specific inputs needed by the cartridge producer saves tremendous time, especially for smaller scale producers (novice/personal users), who do not currently get access to trays, that hold cartridges for filling, in smaller orders. The filling of cartridges and priming for use is much easier when all the necessary critical inputs are all in one tray and can be filled and placed in their correct priming position (upside down) immediately.

Pre-filled cartridge consumers of prefilled cartridges face a similar fate, as they are purchasing largely black-market products that are made with more focus on profit than on providing targeted medicinal effects, for example. Their consumption also results in almost guaranteed (and unnecessary) waste, as pre-filled cartridges are disposed of after use. The present invention enables multiple solutions for a novice/individual filler to create a specific targeted cartridge. Once the filler has sourced an amount of extract (particularly tested/known), the kit designer can then design his kit around the particular medicinal compound he is planning to consume. He can adapt for strength, medicinal needs, flavor, or other factors using the present invention. If their goal is reducing waste but maintaining a pre-manufactured formulation, they can utilize Kit 3.

As a final use case that is highlighted in the present invention, a kit provider (someone with access to tested medicinal compounds; and/or someone with inventory of all other kit components and inputs) can potentially prescribe kits to patients. Just as they may currently prescribe filled cartridges (which may or may not be tested at current). Based on cost structure and consumer preference, many patients/consumers of inhalable cannabinoid (and other) formulations would be able to benefit greatly from solutions highlighted in some of the preferred embodiments.

BRIEF DESCRIPTION OF THE DRAWINGS

The invention may be more readily understood by referring to a number of accompanying drawings in which:

FIG. 5 is a partial exploded view of further components of another embodiment according to the present invention, particularly a cartridge, mouthpiece, and battery pack.

FIG. 6 is a side view of further components of another embodiment according to the present invention, particularly a cartridge, mouthpiece, and cartridge container.

FIG. 9 is a partial exploded view of further components of another embodiment according to the present invention, particularly related to a cartridge, and mouthpiece.

FIG. 10 is a side partial exploded view of further components of another embodiment according to the present invention, particularly related to a mouthpiece, and cartridge.

DETAILED DESCRIPTION OF THE PREFERRED EMBODIMENT

Figure 1:
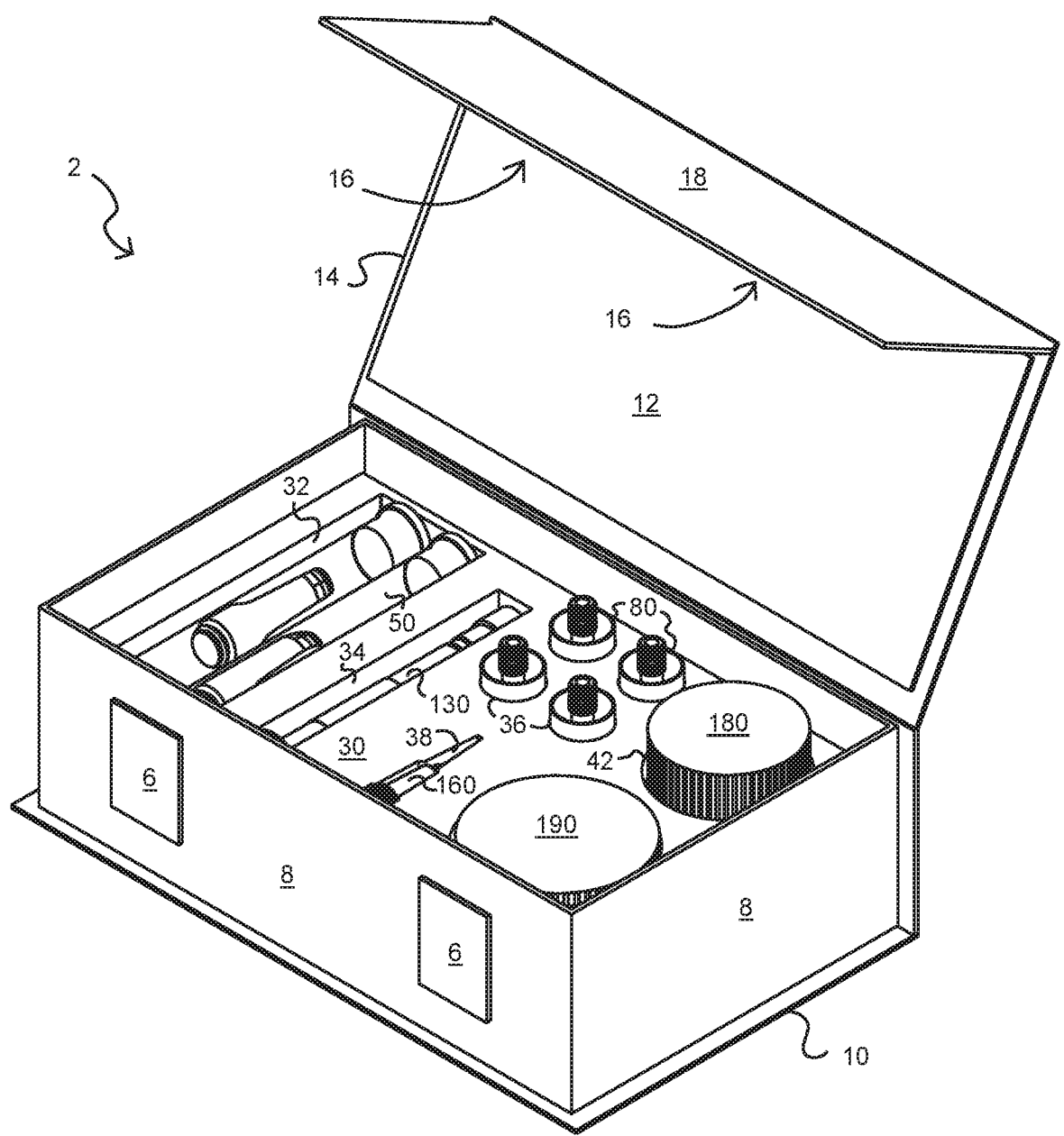
FIG. 1 is a right upper perspective view of a personal vape cartridge manufacturing kit according to one embodiment of the present invention with the lid in a first open position.
Figure 2:
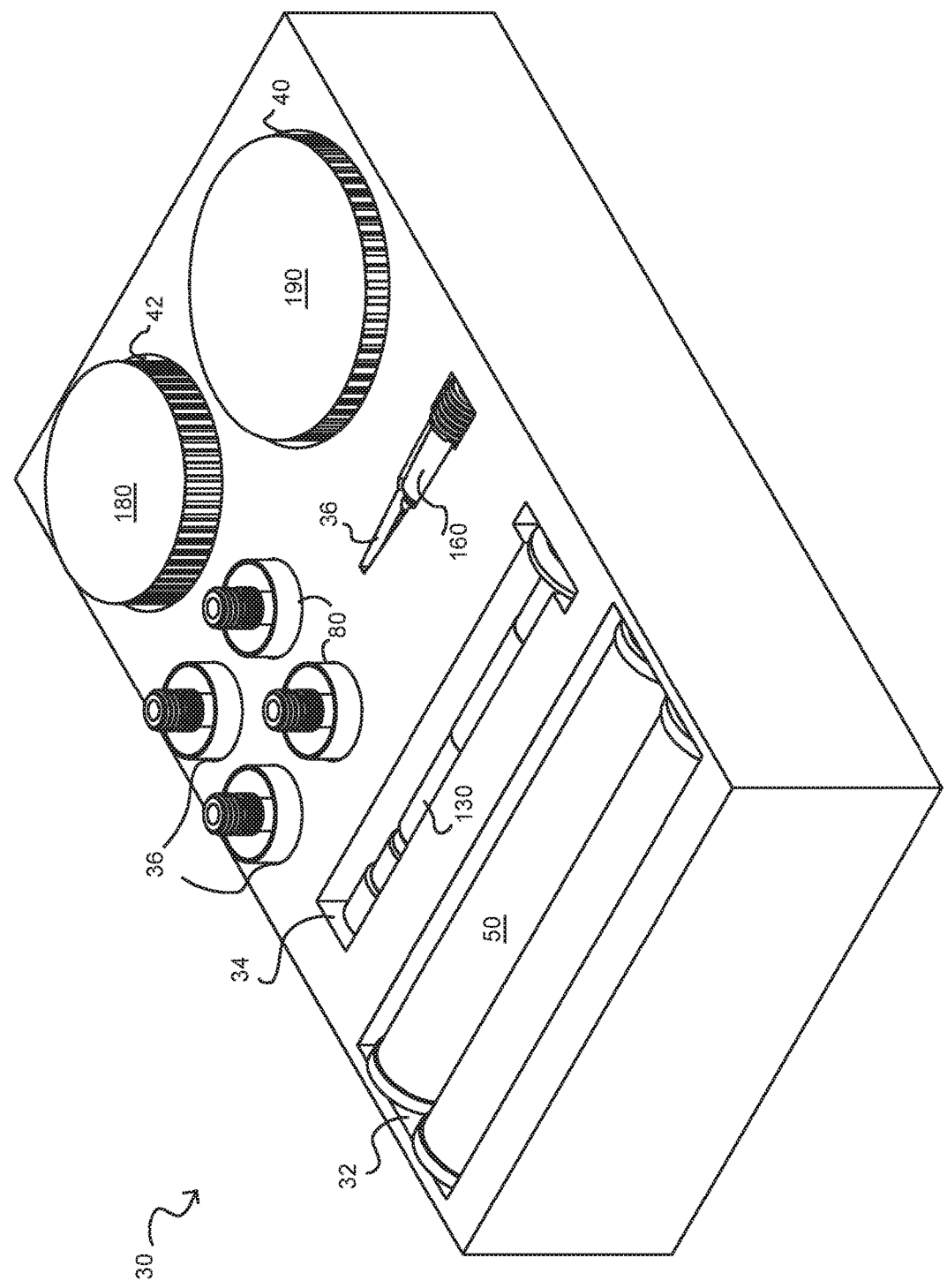
FIG. 2 is a left upper perspective view of the filling station and components of the embodiment in FIG. 1.
Figure 3:
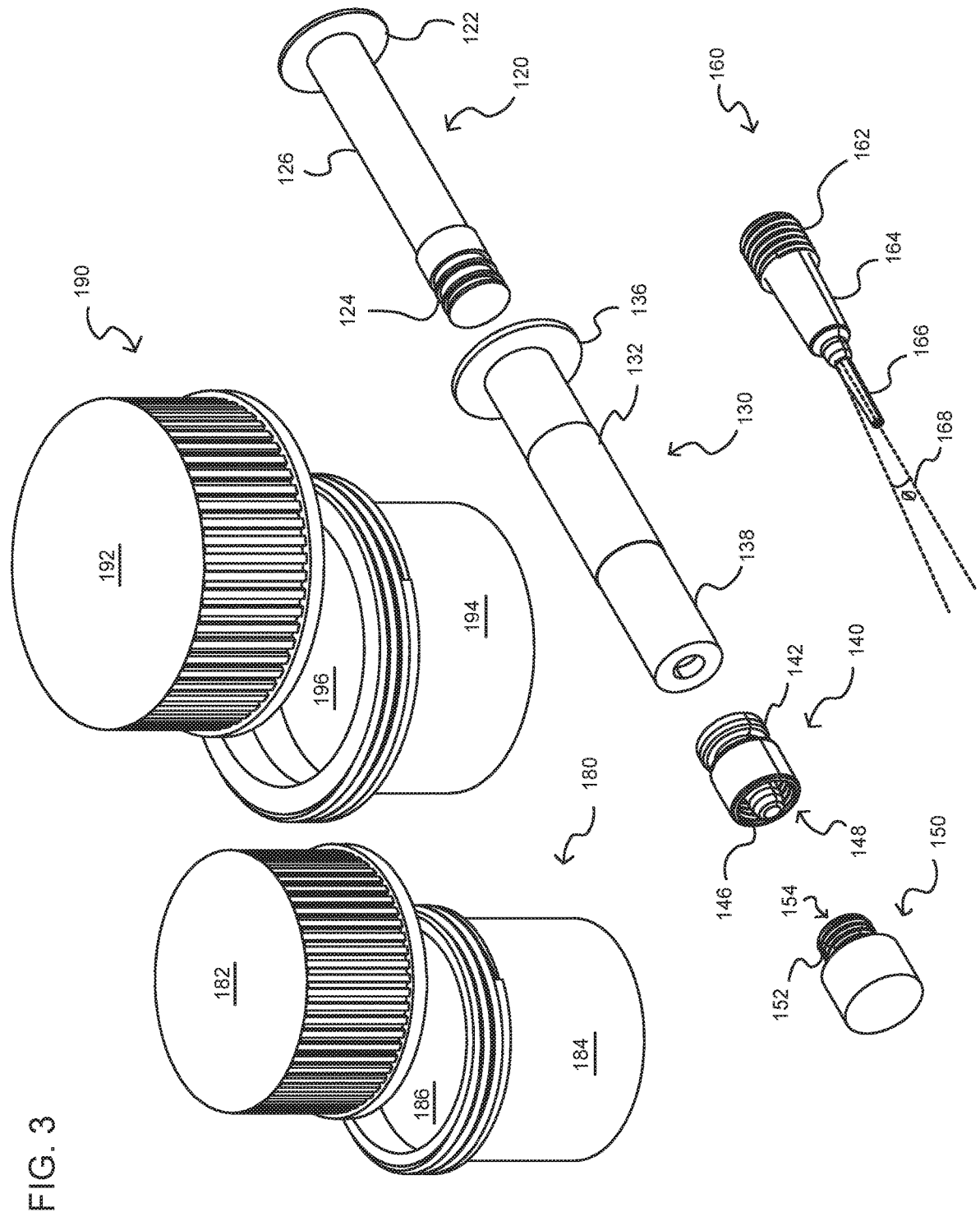
FIG. 3 is an exploded view of some components of the embodiment in FIG. 1, particularly the precision applicator and two containers.
Figure 4:
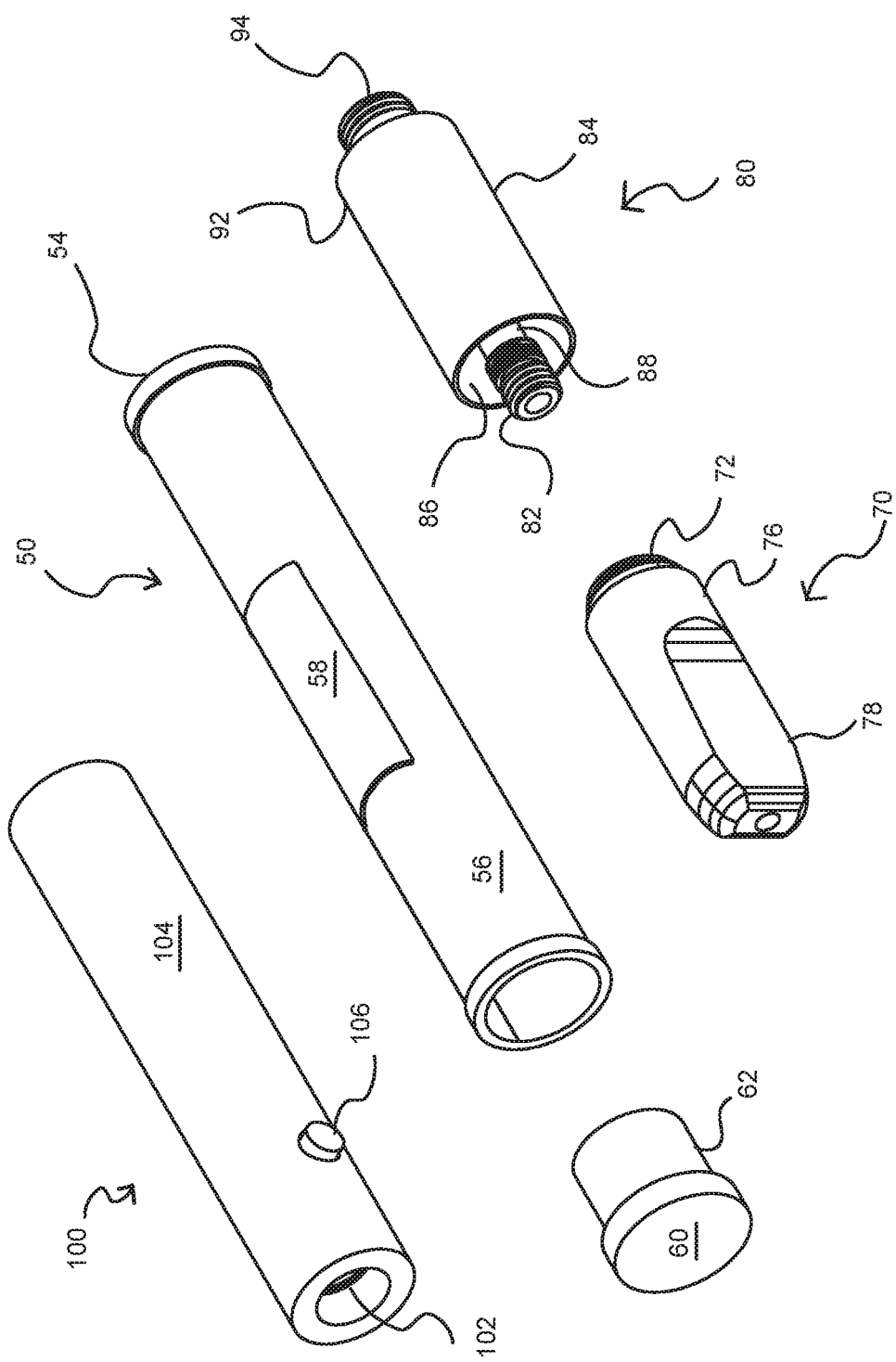
FIG. 4 is a partial exploded view of some further components of the embodiment in FIG. 1, particularly one cartridge, cartridge container, mouthpiece, and battery pack.
Figure 7:
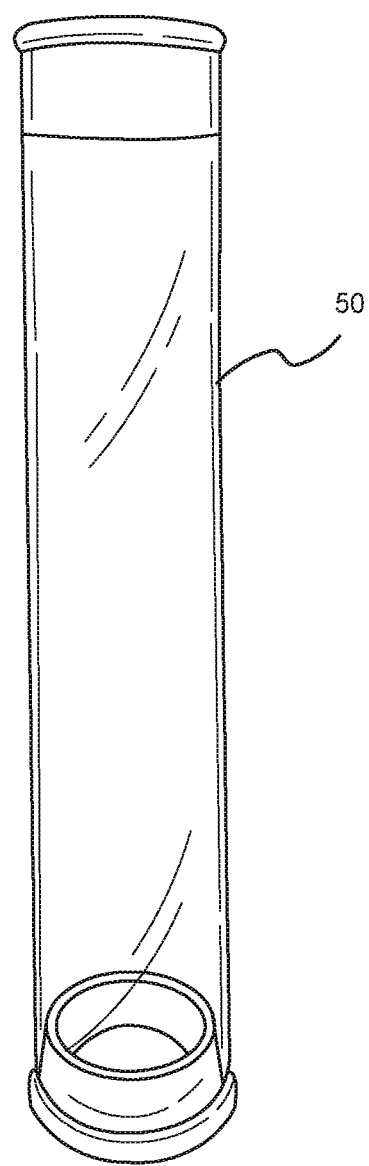
FIG. 7 is a slightly elevated side view of a further cartridge container of another embodiment according to the present invention.
Figure 8:
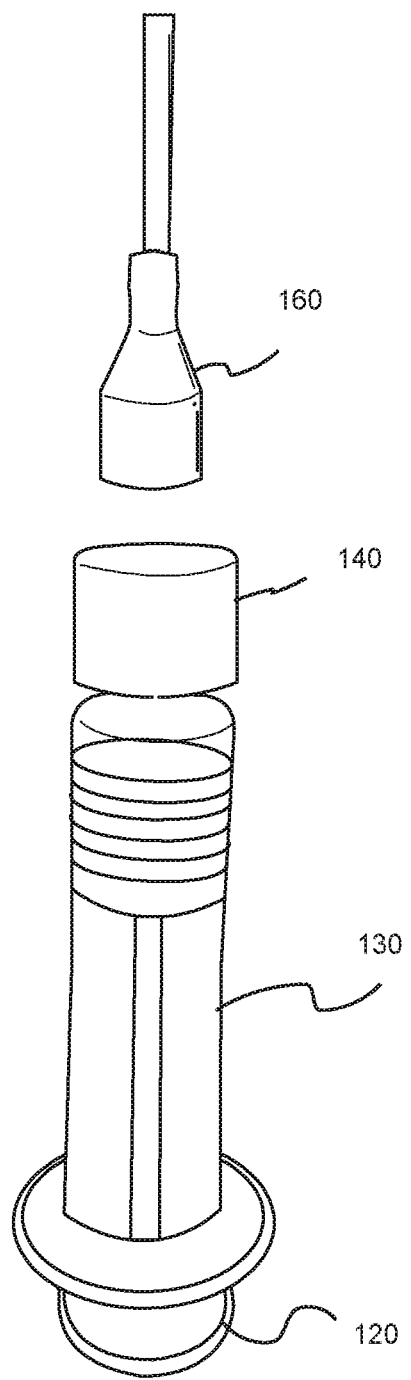
FIG. 8 is a partial exploded view of further components of another embodiment according to the present invention, particularly related to the precision applicator.
Figure 11:
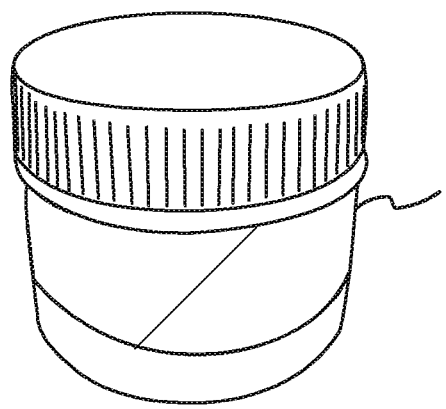
FIG. 11 is a slightly elevated side view of a further component of another embodiment according to the present invention, particularly related to an additive container with warning label.
Figure 13:
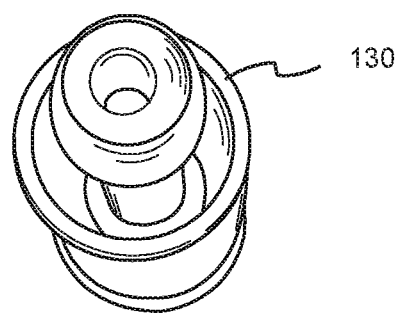
FIG. 13 is an upper slightly perspective view of a further component of another embodiment according to the present invention, particularly related to another type of precision applicator.
Figure 12:
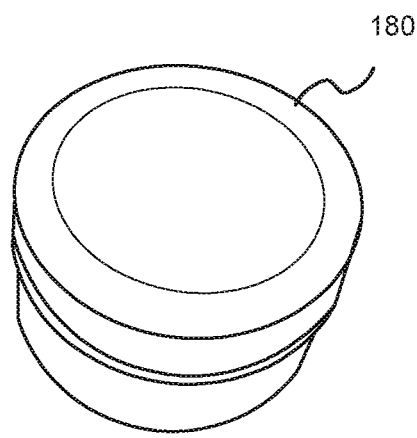
FIG. 12 is a slightly elevated side view of a further component of another embodiment according to the present invention, particularly related to an extract container with content label.
Figure 14:
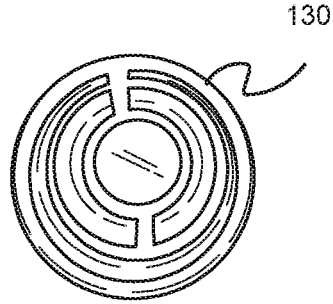
FIG. 14 is a upper view of the precision applicator shown in FIG. 13.
Figure 15:
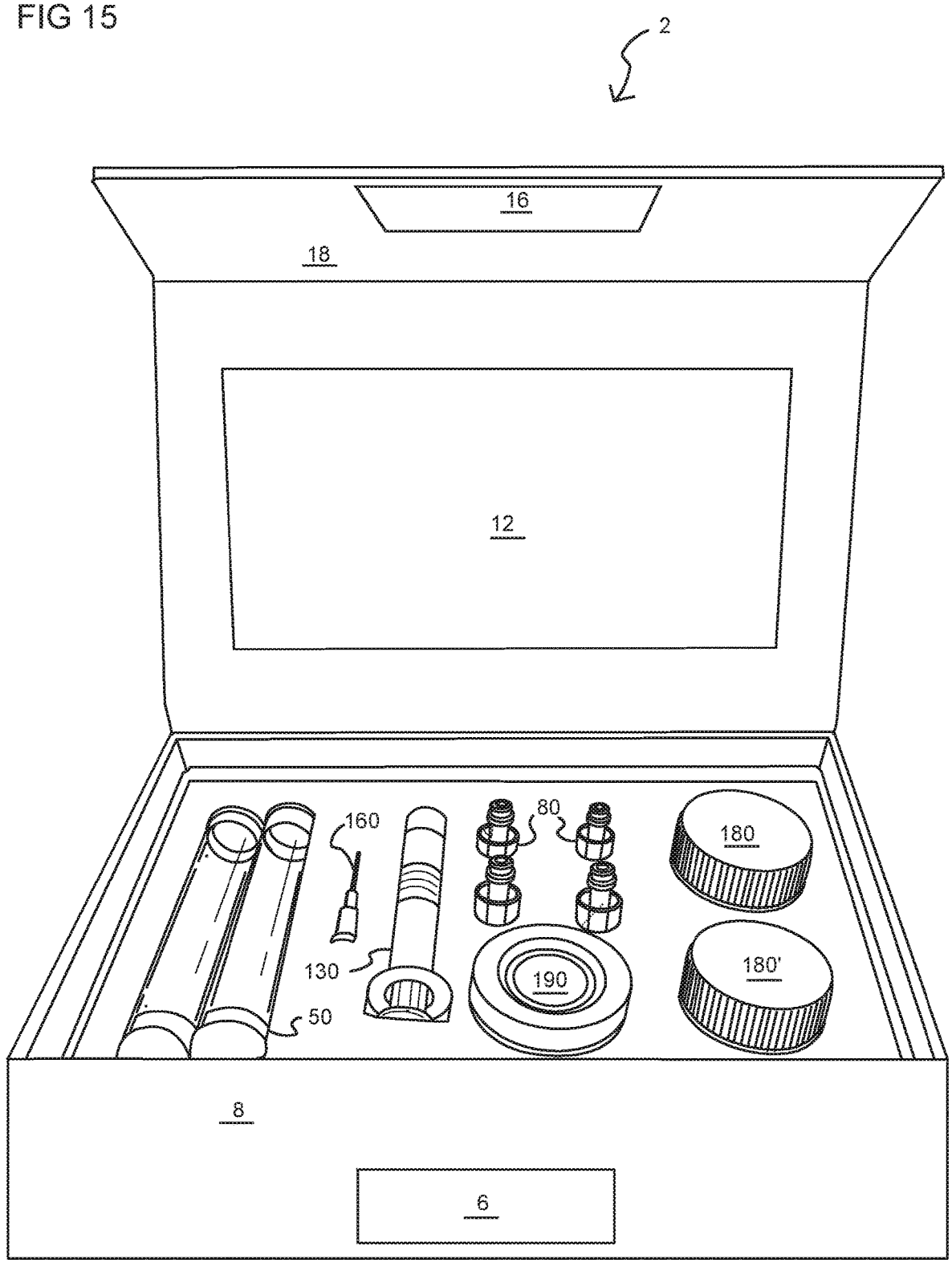
FIG. 15 is an upper front perspective view of a personal vape cartridge manufacturing kit according to another embodiment of the present invention with the lid in a first open position.
Figure 15A:
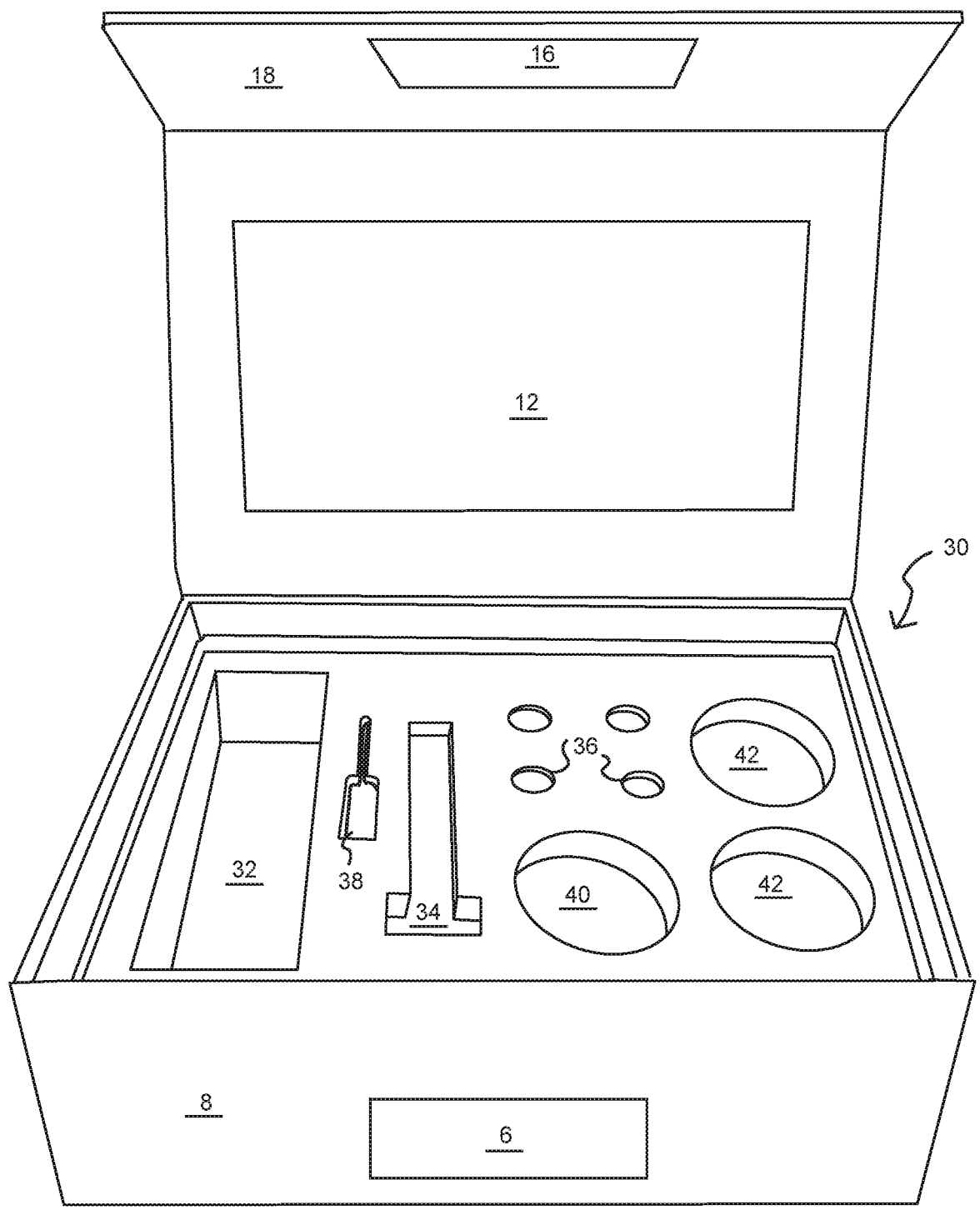
FIG. 15A is a upper front view of the filling station of the kit shown in FIG. 15.
Figure 16:
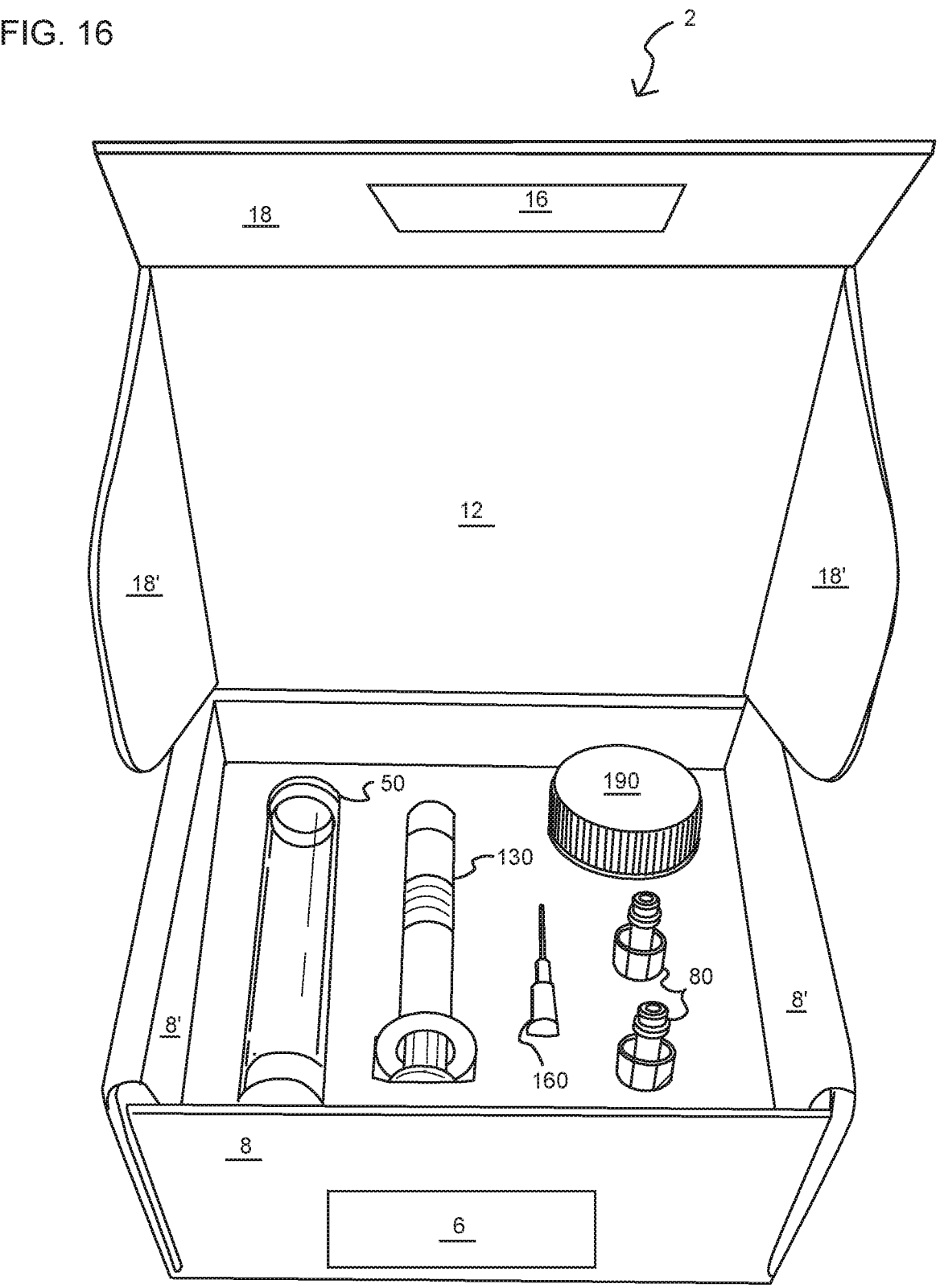
FIG. 16 is an upper front perspective view of a personal vape cartridge manufacturing kit according to another embodiment of the present invention with the lid in a first open position.
Figure 17:
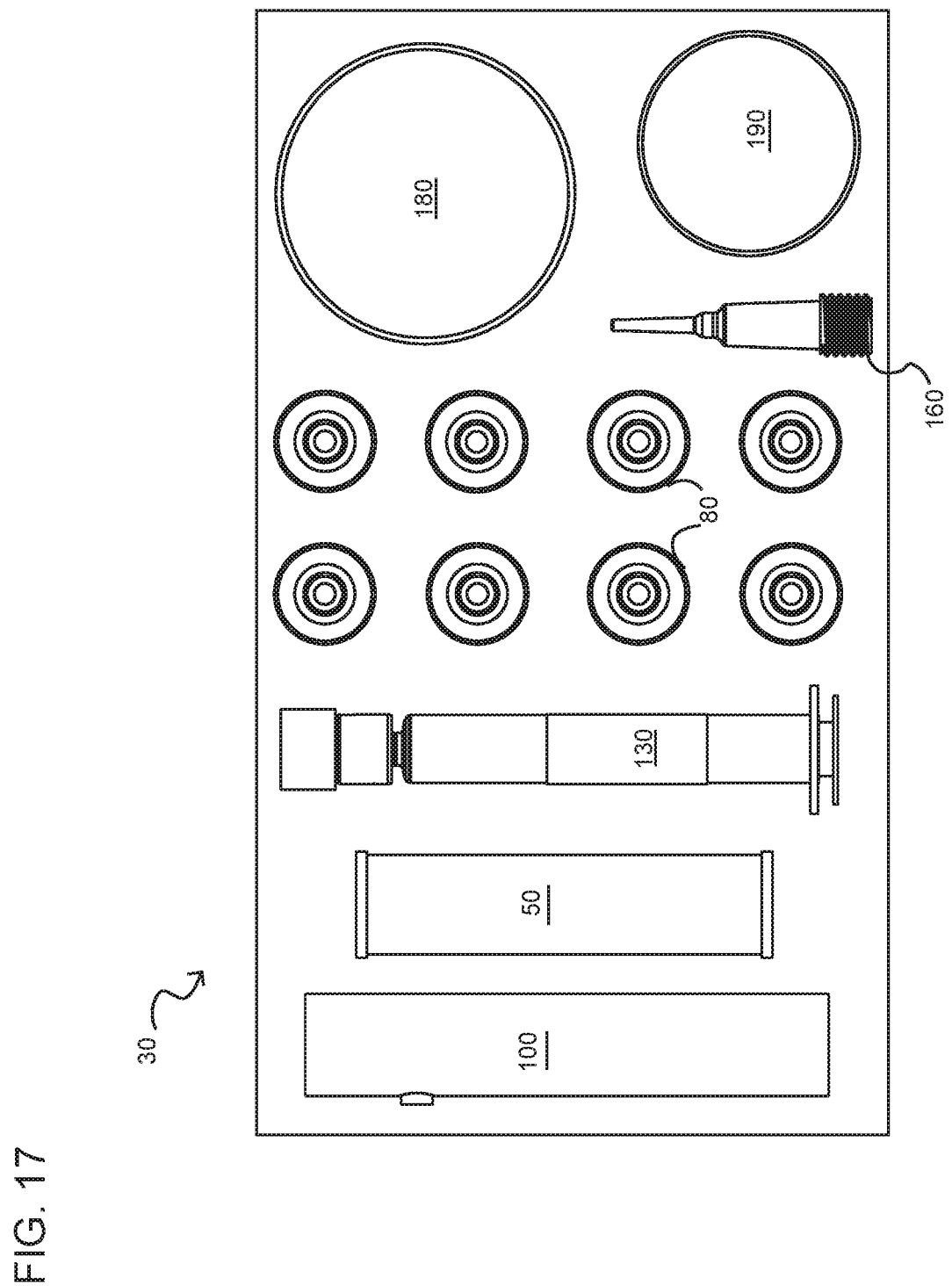
FIG. 17 is an upper view of a further component of another embodiment according to the present invention, particularly related to another type of filling station and associated components.
Figure 18:
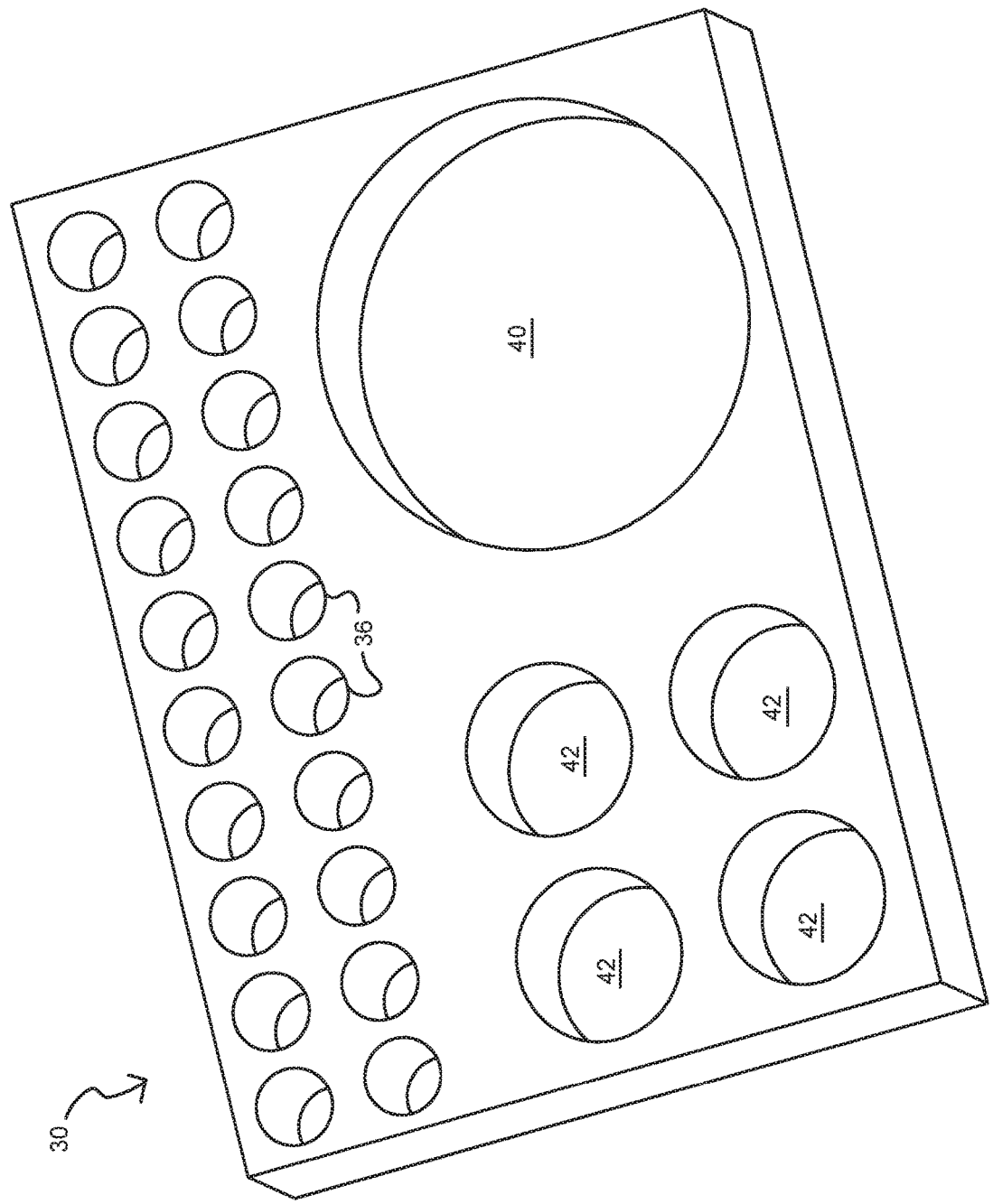
FIG. 18 is an upper right perspective view of a further component of another embodiment according to the present invention, particularly related to another type of filling station.
Figure 19A:
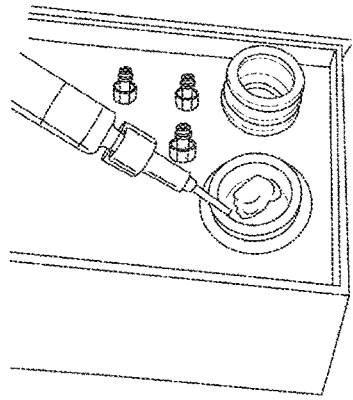
FIGS. 19A-19F are illustrations which may be employed chronologically on a kit to show a method of use according to one embodiment of the present invention.
Figure 19B:
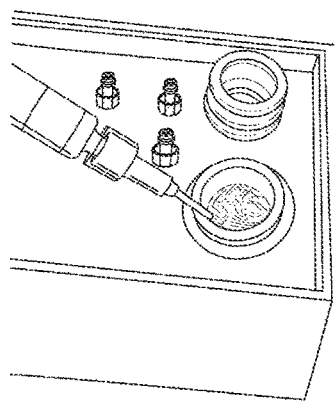
Figure 19C:
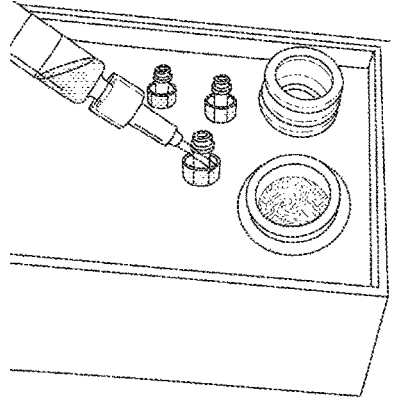
Figure 19D:
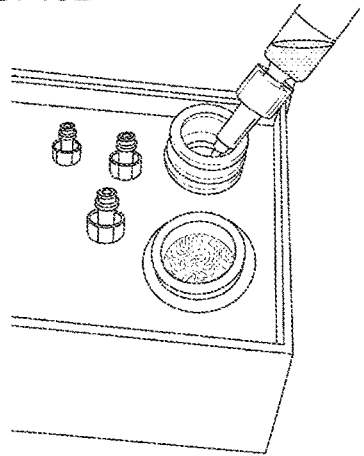
Figure 19E:
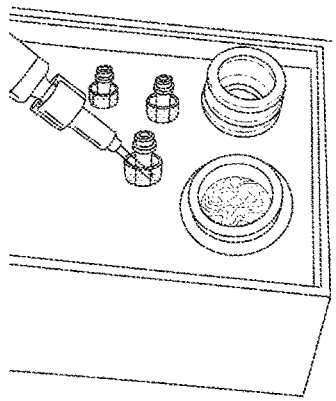
Figure 19F:
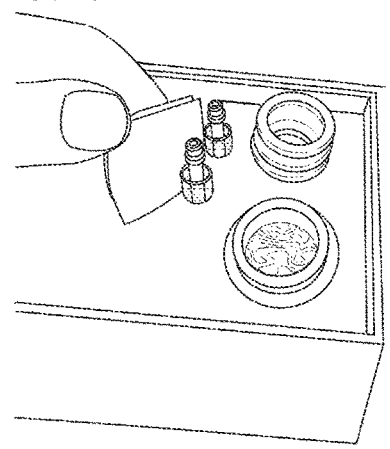

Various aspects of the preferred embodiments of the present invention are illustrated in FIGS. 1-20.

Personal Vape Cartridge Manufacturing Kit #1

FIGS. 1-4 show one embodiment of a kit 2 according to a first embodiment of the present invention. Historically, packages are made to be disposed of and this result in additional waste. The kit 2 according to the embodiment shown here has a multi-purpose reusable container 20 with a number of built-in structural redundancies to facilitates functional characteristics and features of the present invention. Sidewalls 8 extend vertically upwards from a solid base 10 and encompass the main filling station 30 and kit components 50-190. An additional external adjacent sidewall 4 rotatably connects the base 10 to a lid 14, adding increased vertical support and ensuring that even if the lid 14 is somehow compromised, the structural integrity of the main sidewalls 8 remains uncompromised and intact. This is important to prevent wear and tear and to facilitate continued use of at least the filling station 30 as will be discussed further in greater detail later below.

The rotating lid 14 has at least a first position and a second position being rotatable with respect to the external sidewall 4. The rotating lid 14 may have a label 12 provided on either an underside or an outer external side. This label 12 may have identifying information if present on an external side. Alternatively, if provided on an interior side, the label 12 may provide component information, instructions for use 12A having written components 12A, illustrations 12C, and warnings 12D (see, for example, FIG. 20). The rotating lid 14 has at least one pivoting flange 18 (sidewall, lip) opposite the external sidewall 4. This pivoting flange is capable of pivoting or rotating into at least a first position being adjacent to at least one upwardly extending sidewall 8. The flange 18 having a first connection latch 16 positioned so as to engage a corresponding second connection latch 6 on the adjacent upwardly extending sidewall 8. In the embodiment here, the latches 6, 16 are each a pair of magnetic latches, so that the first pair of magnetic latches 16 engages the second pair of magnetic latches, so that casual application of force along the lid 14 is insufficient to open the 14. In other embodiments, the magnetic latches lockingly engage, where the term 'lockingly engage' being used to describe a magnetic force being significant enough to prevent lifting the lid 14 directly upwards by hand, without first rotating the flange 18 away from the sidewall 8. Although the magnetic latches 6, 16 are illustrated as rectangular, these magnetic latches 6, 16 may also be square(s), column(s), or any other correspondingly similar shapes.

Filling Station 30

The filling station 30 serves multiple functions which are not readily apparent to the outside observer but fulfill a vital, and before now, unrecognized imperative for a user. That is, as discussed above, there are any number of products available for inhalable cartridges. However, the inventor has found that customers are unsatisfied with these products for several reasons. The inventor believes that at least one of the reasons that many customers are unsatisfied with the presently available products is the inability to handle the necessary components with ease and security. That is, the inventor believes that kit components 30-190, and particularly the cartridges 80 are of such size and delicacy that mistakes are almost inevitable outside of a laboratory setting where a stray family pet or merely an imbalanced dinner table can quickly spell disaster when trying to mix precise formulations.

The filling station 30 meets these needs by providing secure and stable vertically extending upright holding areas 36 for the cartridges 80, which is to say that a main volume internal axis of the holding areas 36 extends vertically, parallel to the sidewalls. Further ensuring decreased spillage and increased accuracy, the kit 2 also includes vertically extending upright holding areas 40, 42 for the additive container 180 and extract container 190, respectively.

In order to further sustainability goals and reduce waste, this filling station 30 also doubles as a packaging cushion ensuring that all of the kit components are provided with ample shock protection and vibration isolation. To further this goal, the filling station 30 has cushioning holding areas 32, 34, 38 which extend horizontally, which is to say that a main volume internal axis of the holding areas 32, 34, 38 extends horizontally, perpendicular to the sidewalls. These holding areas facilitate securely and releasably retaining at least the cartridge containers 50, precision applicator 130, and in this embodiment, the applicator tip 160 is also separately retained.

In this kit 2, the material of the filling station is a three-dimensional rigid foam form having holding areas with dimensions which are preferably between 5-0.1 micrometers, and more preferably at least 2 micrometers smaller than the respective components they are designed to hold. This ensures that the resultant interference fit between the kit components and their respective holding areas is sufficient to create a frictional force sufficient to overcome a respective gravitational force if the kit 2 was inadvertently rotated into an upside-down position, i.e., in which the openings of the holding areas are facing downwards. Thus, the contents of the kit 2 remain securely retained in the filling station regardless of whether the lid 14 is securely fastened. This provides yet another structural redundancy, to improve overall functionality as discussed above.

Cartridge Containers 50

The cartridge containers 50 are generally columnar containers capable of storing both the individual cartridges 80 and a respective mouthpiece 70. The columnar walls 56 extend downwards to a rigid base 54 around an internal cavity 52. A label 58 is provided along the side of the wall 56 with identifying information such as the type of mouthpiece 70, and the type of cartridge 80. Other embodiments have erasable labels 58 when the cartridges 80 have storable fluid contained within, so that the identifying information for these cartridge containers 50 can also indicate the date that the cartridge 80 was filled. The lid 60 of the cartridge containers 50 has a circumferential mating edge 62 so that when the lid is closed, the upper lip of the columnar wall 56 is sealingly engaged to the mating edge 62 preventing leaks or spills.

Cartridges 80

The cartridges 80 of this kit have a mouthpiece 70, atomizer 90, and the main chamber 84. The holding chamber cavity 86 of the main chamber 84 is preferably capable of holding between about 10 mL to about 100 mL, more preferably between about 20 mL to about 60 mL, and more preferably, about 40.5 mL. At a first lower end, the atomizer 90, has a threaded base 94 capable of engaging a threaded portion 102 of the battery pack 100. A metal ring 92 supports the base of the glass tube of the main chamber 84 which surrounds the atomizer 90. A hollow shaft 88 connects the atomizer 90 with the mouthpiece 70 via the connection ring 82. The atomizer 90 of this cartridge has large carborator flow ports and porous ceramic core with an infused coil heating element.

The mouthpieces 70 of the kit 2 have an adapter 72 capable of matingly engaging their corresponding cartridge main chambers 84. A bore 74 extends throughout the interior of the mouthpiece 70 from a first end of the adapter 72 to a second end of the beak 78. The beak has a generally sloping shape which extends gradually from the main shank 76.

After filling, the mouthpiece 70 is connected to the cartridge main chamber 84, and sealingly engages a first end of the cartridge main chamber 84. As suction is required in order to break the seal once the main chamber 84 is connected to the mouthpiece 70, the mouthpieces 70 are often used as seals for filled cartridges 80.

The kit 2 may also be provided with a battery pack 100 which may be housed in the filling station 30 holding space 32 adjacent the cartridge containers of similar columnar build and shape. The battery packs 100 have a basic columnar shaft 104 with a cartridge adapter 102 and power switch 106.

Precision Applicator 130

The precision applicator of the present kit 1 has several components including the plunger 120, barrel 130, hub 140, the cap 150, and the applicator tip 160. For obvious reasons, the cap 150 and the applicator tip 160 cannot both be attached at the same, but instead are alternately attachable to the hub 140. The plunger 120 has a plunger flange 122 at a first end of a main shaft 126. At the opposite end of the main shaft 126 is a seal 124 which internally engages the inside walls of the cylindrical hollow shaft 138 of the barrel 130. Indicia 132 along the outer walls of the cylindrical hollow shaft 138 ensure that precise measurements can be achieved outside of laboratory conditions. A barrel flange 136 extends horizontally outward from the outer walls of the cylindrical hollow shaft 138 at an end opposite the hub 140.

The hub 140 has a main cylindrical portion 142, having a first diameter meeting the end of the barrel shaft 138, then narrowing drastically, and having a second diameter being less than 5/7 of the first diameter. A flange outwardly extends from the main cylindrical portion 142 before bending and forming an outer sleeve 144 surrounding the main cylindrical portion 142 along the second smaller diameter portion. A cylindrical gap 148 exists between the outer sleeve 144 and the second smaller diameter portion of the main cylindrical portion 142. The outer sleeve 144 has a threaded inner wall 146 facilitating a locking engagement with either the cap 150 or the applicator tip 160. The cap 150 has a corresponding threaded wall 152 capable of engaging with the threaded inner wall 146 of the hub 140. The cap also has a hollow space 154 capable of receiving the second smaller diameter portion of the main cylindrical portion 142 extending upwards from the joining point of the outer sleeve 144. In some embodiments, the hub 140 may comprise a luer lock capable of facilitating a locking engagement seal with either the applicator tip 160 or the cap 150.

The applicator tip 160 is similar in some respects to a typical needle head, in that the device is mainly hollow, providing a channel to provide fluids to a specific area. An adapter 162, a needle hub 164, and main shaft 166 are all hollow, their internal channels internally connected. However, unlike most needle tips, the internal channels are not all coaxially aligned. Instead, the internal axis of the main shaft 166 is at a slight angle 168, juxtaposed from the internal axis of the needle hub 164, and the adapter 162. Also distinct from other injectors, the gauge is both rather small, i.e., 5-20 gauge, and more preferably, about 7-12 gauge (large diameter) with a blunt tip.

Additives 180 & Extracts 190

The additive container 180 and extract container 190 are securely retained by the filling station 30 in upright holding areas 40, 42, respectively. The extract container 190, also called mixing container, is generally larger than 'necessary' in order to facilitate mixing with the stirring rod. The height of the filling station is such that the lids 182, 192, may be removed while the filling station holding areas 40, 42 still retain the bases 184, 194 securely. This ensures that the additive and extract materials 186, 196 within are not subject to jostling which may cause material loss. The lids 182, 192 may be labeled according to their internal content, and/or comprise additional identifying information. For example, 500 mg cartridges, having a formula with 75% extract and 25% additive, may have a label indicating the medicinal profile and potential effects including side effects: 337.5 mg THC-A, mood enhancer; 50 mg limonine terepenes, appetite, pain relief. The corresponding kit 2 identifying information might also have a producer name; state issued license number and other required info including but not limited to the extract potency: 90% THC-A; and the name and location of the testing facility.

Further Features and Embodiments

As discussed in the summary of the invention above, the present invention seeks to provide options for various kits and use. As these variations and the reasoning behind these variations are discussed above in the summary, it is believed that no further discussion of these structural variations which are plainly visible in the appended drawings is necessary, but a brief summary is provided here again. FIGS. 5-14 illustrate various aspects of these components which are tailored for specific uses and needs identified by the inventors. Specifically, FIGS. 5-14 illustrate various adapted cartridges 80, mouthpieces 80, battery packs 100, cartridge containers 50, precision applicators 130, additives 180, and extracts 190.

For example, FIG. 6 illustrates the cartridge 80 having a shorter main chamber 84 and correspondingly shorter holding chamber cavity 86 and hollow shaft 88. Whereas FIGS. 9-10 illustrates the cartridge 80 having a longer main chamber 84 and correspondingly longer holding chamber cavity 86 and hollow shaft 88. The internal length of the main chamber 84 of earlier embodiments being preferably between 1-3 cm, and more preferable about 1.5 cm. The internal length of the main chamber 84 of shorter embodiments being preferably between 0.5-2 cm, and more preferable about 1 cm. The internal length of the main chamber 84 of longer embodiments being preferably between 2-5 cm, and more preferable about 3.5 cm.

Figure 20:
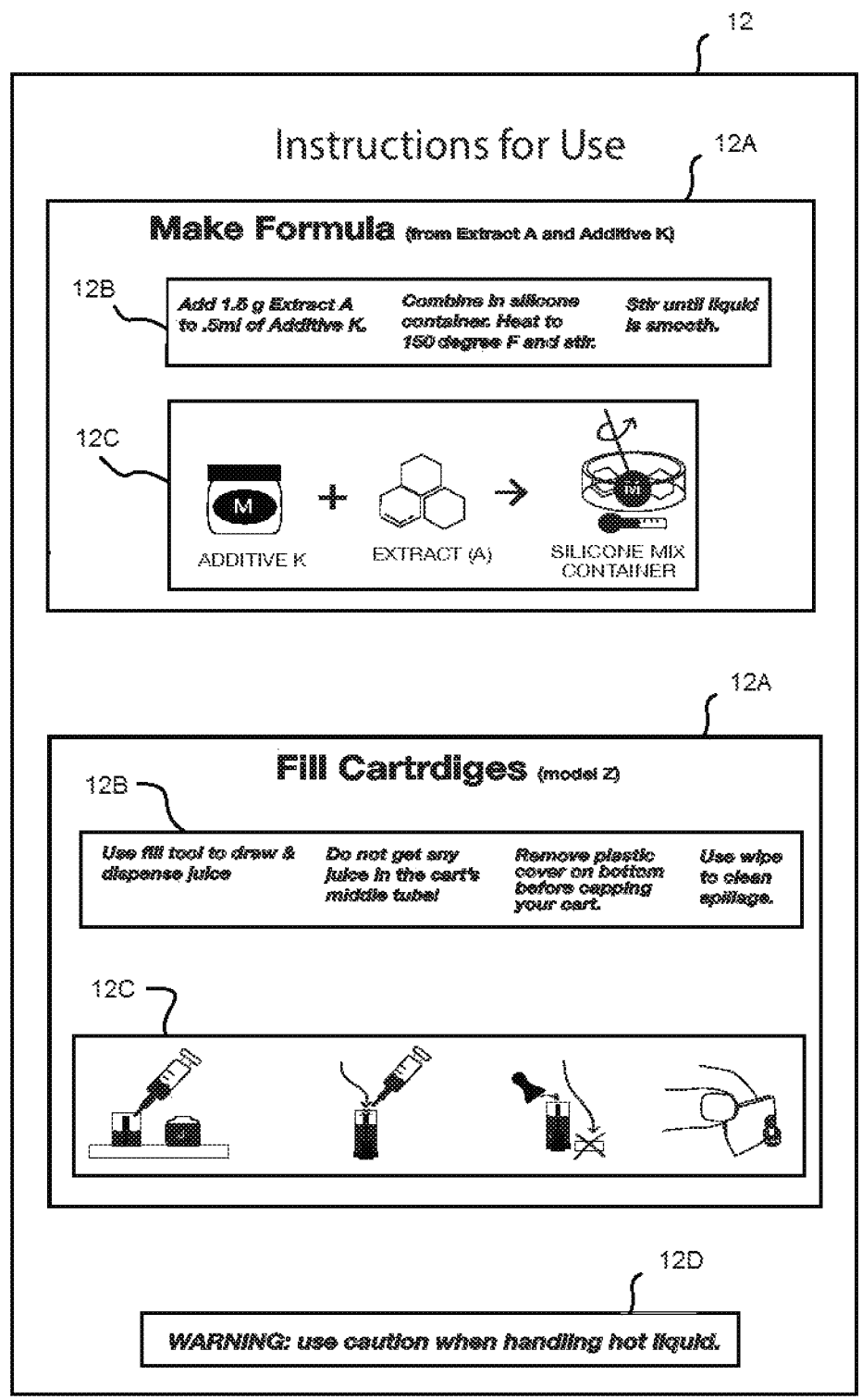
FIG. 20 is an example illustration showing a potential method of use of one embodiment according to the present invention.

FIGS. 9-10 show alternate cartridges 80 which work in concert with the filling station in FIG. 20 by eliminating the requirement for a cartridge container 50. This is made possible by having end caps which provide a further structural redundancy and sealingly engage a second end of the cartridge 80 opposite the mouthpiece 70. This embodiment also employs end caps which sealingly engage the first end of the main chamber 84, these end caps are structurally identical to a first portion of the mouthpieces 70 lacking only the beak 78 and have an adapter 72 capable of matingly engaging a corresponding cartridge main chamber 84. A bore 74 extends partially throughout the interior shank 76 of the end cap from a first end of the adapter 72 so as to accommodate and engage with connection rings 82 of the hollow shaft 88 which extend upward from beyond a peripheral edge of the walls of the main chamber 84.

FIGS. 15-18 illustrate various kits 2 and filling stations 30 to facilitate various unmet needs as discussed in the summary above. FIGS. 19A-19F are illustrations which may be employed chronologically on a kit to show a method of use according to one embodiment of the present invention. FIG. 20 is an example illustration showing a label 12 having various components 12A, written instructions 12B, associated diagrammatical illustrations 12C, and associated warnings 12D according to the present invention as discussed above.

LIST OF REFERENCED ELEMENTS

The following reference numbers are adhered to within the specification to refer to those referenced elements within the drawings of the present application.

kit 2
external adjacent sidewall 4
magnetic latches 6, 16
sidewalls 8
solid base 10
label 12
label subcomponents 12A
written instructions 12B
diagrammatical illustrations 12C
warnings 12D
rotating lid 14
pivoting flange 18
reusable container 20
main filling station 30
horizontal holding areas 32, 34, 38
vertical holding areas 36, 40, 42
cartridge containers 50
internal cavity 52
rigid base 54
columnar walls 56
label 58
lid 60
mating edge 62
internal cavity 64
mouthpiece 70
adapter 72
bore 74
shank 76
beak 78
cartridges 80
connection ring 82
main chamber walls 84
holding chamber cavity 86
hollow shaft 88
atomizer 90
threaded base 94
metal ring 92
threaded portion 102
battery pack 100
plunger 120
plunger flange 122
seal 124
main shaft 126
barrel 130
indicia 132
barrel flange 136
hollow shaft 138
hub 140
main cylindrical portion 142
outer sleeve 144
threaded inner wall 146
inner gap 148
cap 150
threaded wall 152
hollow space 154
applicator tip 160
adapter 162
needle hub 164
main shaft 166
angle 168
additive container 180
lid 182
base 184
extract container 190
lid 192
base 194
extract 196

CONCLUSION

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A vape cartridge filling kit comprising:

a reusable container having: a sidewall extending vertically upwards from a solid base, the sidewall having a first connection latch; a lid being rotatable with respect to the sidewall from a first open position to a second closed position, the lid having a second connection latch; the first connection latch and second connection latch respectively positioned on the sidewall and lid so as to engage one another when the lid is in the second closed position; and at least one structural redundancy;

a filling station which is encompassed by the sidewall and base of the reusable container when the lid is in the first open position, and further encompassed by the lid when the lid is in the second closed position; the filling station having: a plurality of vertical holding areas which extend vertically and parallel to the sidewall; and a plurality of horizontal holding areas which extend horizontally and perpendicular to the sidewall;

a plurality of cartridges, each of the plurality of cartridges having an atomizer and a main chamber; a height of each of the plurality of cartridges being less than a height of the sidewall; a diameter of each of the plurality of cartridges forming an interference fit when each of the plurality of cartridges is positioned within a respective one of the plurality of vertical holding areas; and a precision applicator having a diameter capable of forming an interference fit when the precision applicator is positioned in a respective one of the plurality of horizontal holding areas.

2. The vape cartridge filling kit of claim 1 wherein the at least one structural redundancy consisting of:

a first portion of the base of the reusable container extending for a first distance beyond a first portion of the sidewall, and a second portion of the base extending for a second distance beyond a second portion of the sidewall;

a first portion of a main body of the lid extending for the first distance beyond the first portion of the sidewall, and a second portion of the main body of the lid extending for the second distance beyond the second portion of the sidewall, when the lid is in the second closed position;

an additional sidewall externally adjacent to the first portion of the sidewall, and the additional sidewall extending vertically upwards between the first portion of the base and the first portion of the main body of the lid;

a lid flange pivotably connected to the second portion of the main body of the lid, the lid flange having a first pivoting position and a second pivoting position, such that when the lid is in the second closed position and the lid flange is in the second pivoting position, the lid flange is externally adjacent to the second portion of the sidewall, and the lid flange extends vertically downwards from the second portion of the main body of the lid towards the second portion of the base;

the first distance accommodating the width of the additional sidewall; and the second distance accommodating the width of the lid flange.

3. The vape cartridge filling kit of claim 1 wherein:
the first connection latch consists of a first pair of magnetic latches being positioned on the sidewall;
the second connection latch consists of a second pair of magnetic latches being positioned on a lid flange having a first pivoting position and a second pivoting position; and
when the lid is in the second closed position and the lid flange is in the second pivoting position, the second pair of magnetic latches lockingly engages the first pair of magnetic latches.

4. The vape cartridge filling kit of claim 1 wherein the reusable container having a label positioned provided on one of an under side and an external side of the lid, and the label comprising at least one of identifying information, component information, instructions for use, warnings, written components, and illustrating diagrams.

5. The vape cartridge filling kit of claim 1 further comprising:
at least one additive container securely containing at least one additive selected from the group consisting of solvent, terpenes, met oils, and propylene glycol/glycerol (PG/VG);
at least one extract container securely containing at least one extract selected from the group consisting of tetrahydrocannabinol (THC) and cannabidiol (CBD) cannabinol (CBN), cannabigerol (CBG), and cannabichromene (CBC);
at least one precision applicator with measuring indicia for providing a specific amount of the at least one additive, and the at least one extract container to one of the plurality of cartridges.

6. A method for filling cartridges using a kit, the kit comprising:
providing a kit having: a reusable container having a lockable lid; at least one structural redundancy; a filling station having a plurality of vertical holding areas and a horizontal holding area; a plurality of cartridges and a plurality of containers, each held via interference fit in one of the plurality of vertical holding areas; each of the plurality of containers securely containing a pre-measured amount of one of an active compound and an inactive compound; and a precision applicator held via interference fit in the horizontal holding area;
using measuring indicia on the precision applicator to withdraw a first calculated amount of the in-active compound;
using measuring indicia on the precision applicator to withdraw a second calculated amount of the active compound;
preparing a personalized formulation by mixing the first calculated amount of the in-active compound and the second calculated amount of the active compound in one of the plurality of containers;
using measuring indicia on the precision applicator to withdraw a third calculated amount of the personalized formulation;
filling a holding chamber cavity of the cartridge with personalized formulation while simultaneously avoiding filling a hollow shaft of the cartridge; and securely holding each of the plurality of cartridges and plurality of containers, by maintaining each respective position in the plurality of vertical holding areas.

7. A reusable container for vape cartridge filling comprising:
a sidewall extending vertically upwards from a solid base, the sidewall having a first connection latch;
a lid being rotatable with respect to the sidewall from a first open position to a second closed position, the lid having a second connection latch; the first connection latch and second connection latch respectively positioned on the sidewall and lid so as to engage one another when the lid is in the second closed position;
a filling station which is encompassed by the sidewall and base of the reusable container when the lid is in the first open position, and further encompassed by the lid when the lid is in the second closed position;
a plurality of vertical holding areas which extend vertically and parallel to the sidewall;
a plurality of horizontal holding areas which extend horizontally and perpendicular to the sidewall; and
a plurality of cartridges, each of the plurality of cartridges having an atomizer and a main chamber; a height of each of the plurality of cartridges being less than a height of the sidewall; a diameter of each of the plurality of cartridges forming an interference fit when positioned in a respective one of the plurality of vertical holding areas.

* * * * *